United States Patent
Basilion et al.

(10) Patent No.: US 10,434,194 B2
(45) Date of Patent: *Oct. 8, 2019

(54) PSMA TARGETED NANOBUBBLES FOR DIAGNOSTIC AND THERAPEUTIC APPLICATIONS

(71) Applicant: CASE WESTERN RESERVE UNIVERISTY, Cleveland, OH (US)

(72) Inventors: James R. Basilion, Shaker Heights, OH (US); Agata Exner, Westlake, OH (US); Xinning Wang, Cleveland, OH (US); Christopher Hernandez, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/691,407

(22) Filed: Aug. 30, 2017

(65) Prior Publication Data
US 2018/0064831 A1 Mar. 8, 2018

Related U.S. Application Data

(63) Continuation-in-part of application No. 13/825,941, filed on Jun. 20, 2013, and a continuation-in-part of application No. 14/767,984, filed on Aug. 14, 2015, now Pat. No. 9,889,199, and a continuation-in-part of application No. PCT/US2017/035766, filed on Jun. 2, 2017.

(60) Provisional application No. 62/381,144, filed on Aug. 30, 2016.

(51) Int. Cl.
*A61K 49/22* (2006.01)
*A61B 8/08* (2006.01)
*C08L 33/26* (2006.01)
*C08L 71/08* (2006.01)
*C08K 5/21* (2006.01)

(52) U.S. Cl.
CPC ............ *A61K 49/223* (2013.01); *A61B 8/481* (2013.01); *A61K 49/227* (2013.01); *C08K 5/21* (2013.01); *C08L 33/26* (2013.01); *C08L 71/08* (2013.01); *C08G 2650/58* (2013.01); *C08L 2201/06* (2013.01); *C08L 2203/02* (2013.01)

(58) Field of Classification Search
CPC combination set(s) only.
See application file for complete search history.

(56) References Cited

U.S. PATENT DOCUMENTS

| 6,572,840 | B1 | 6/2003 | Toler |
|---|---|---|---|
| 7,452,551 | B1 | 11/2008 | Unger et al. |
| 8,119,163 | B2 | 2/2012 | Devane et al. |
| 8,246,968 | B2 | 8/2012 | Zale et al. |
| 9,193,763 | B2 | 11/2015 | Low et al. |
| 9,320,757 | B2 | 4/2016 | Exner et al. |
| 2003/0003055 | A1 | 1/2003 | Unger et al. |
| 2008/0193381 | A1 | 8/2008 | Babich et al. |
| 2008/0311045 | A1 | 12/2008 | Hardy |
| 2010/0324008 | A1* | 12/2010 | Low .................... A61K 49/0041 514/184 |

FOREIGN PATENT DOCUMENTS

| WO | 2008/057437 A1 | 5/2008 |
|---|---|---|
| WO | 2011/106639 A1 | 9/2011 |
| WO | 2012/106713 A2 | 8/2012 |

OTHER PUBLICATIONS

Feshitan, Jameel A., et al., "Microbubble size Isolation by differential Gentrification", Journal of Colloid and Interface Science 329 (2009) 316-324.
Liu, Riu, et al., "The Preparation and Characterization of gas bubble containing liposomes", 2005 IEEEEngineering in Medicine and Biology 27th Annual Conference, Shanghai; p. 3998-4001.
Yin, Tinghui, et al., "Nanobubbles for enhanced ultrasound imaging of tumors", International Journal of Nanomedicine, 2012:7 895-904.
Unger, Evan C., et al., "Therapeutic Applications of Lipid-coated microbubbles", Advanced Drug Delivery Reviews 56 (2004) 1291-1314.
Krupka, Tianyi, et al., "Formulation and Characterization of Echogenic Lipid-Pluronic Nanobubbles", vol. 7, No. 1, 49-59, Molecular Pharmaceutics.
Unger, Evan, et al., "Acoustically Active Lipsoheres Containing Paclitaxel: A New Therapeutic Ultrasound Contrast Agent", Investigative Radiology, vol. 33(12), Dec. 1998, p. 886-892.
Oh, Kyung, et al., "Micellar Formulations for Drug Delivery based on mixtures of hydrophobic and hydrophilic Pluronic block copolymers", Jounal of Controlled Release 94 (2004) 411-422.
Krupka, Tianyi M., et al., "Formulation and Characterization of Echogenic Lipid-Pluronic Nanobubbles", Mol. Pharm. Feb. 1, 2010; 7(1): 49-59.
European Search Report dated Oct. 10, 2016.
Kularatne, Sumith, et al., "Synthesis and Biological Analysis of Prostate-Specific Membrane Antigen-Targeted Anticancer Prodrugs", J. Med. Chem. 2010, 53, 7767-7777.
Ikeda, Masato, et al. "Supramolecular hydrogel capsule showing prostate specific antigen-responsive function for sensing and targeting prostate cancer cells", Chem. Sci., 2010, 1, 491-498.

* cited by examiner

*Primary Examiner* — Yong L Chu
(74) *Attorney, Agent, or Firm* — Tarolli, Sundheim, Covell & Tummino LLP

(57) ABSTRACT

A PSMA targeted nanobubble includes a membrane that defines at least one internal void, which includes at least one gas, and at least one PSMA ligand coupled or conjugated to the membrane. The membrane includes at least one lipid and at least one nonionic triblock copolymer that is effective to control the size of the nanobubble without compromising in vitro and in vivo echogenicity of the nanobubble.

18 Claims, 11 Drawing Sheets

Statistical analysis is done by student's t-test where **P<0.01

D.

Time after PSMA-IR800 injection

PSMA TARGETED NANOBUBBLES FOR DIAGNOSTIC AND THERAPEUTIC APPLICATIONS

RELATED APPLICATION

This application is a Continuation-in-Part of U.S. patent application Ser. No. 13/825,941, filed Jun. 20, 2013, Ser. No. 14/767,984, filed Aug. 14, 2015, now U.S. Pat. No. 9,889,199 and PCT/US2017/035766, filed Jun. 2, 2017. This application also claims priority from U.S. Provisional Application No. 62/381,144, filed Aug. 30, 2017, the subject matter of which are incorporated herein by reference in their entirety.

GOVERNMENT FUNDING

This invention was made with government support under Grant No. W81XWH-16-1-0371 awarded by The Department of Defense/Army Medical Research and Material Command. The United States government has certain rights in the invention.

TECHNICAL FIELD

This application relates to diagnostic and therapeutic compositions, and more particularly to targeted nanobubbles for diagnostic, therapeutic, and theranostic applications.

BACKGROUND

Ultrasound contrast agents (UCA) are small gas-filled bubbles with a stabilizing shell made from a variety of materials, such as polymer, protein or lipid. Other than the traditional applications of these agents in diagnostic ultrasound imaging, UCA have found relevance in therapeutic applications including targeted gene and drug delivery. These adaptable particles are currently being explored as protective therapeutic carriers and as cavitation nuclei to enhance delivery of their payload by sonoporation. Together these functions improve payload circulation half-life and release profiles as well as tissue selectivity and cell uptake. Regardless of the mode of action, it is advantageous, particularly in cancer therapy, for the bubbles to extravasate from the vasculature and arrive at the cellular target site for the desired effect.

Commercial UCA available today are typically designed to serve only as blood pool agents with diameters of 1-8 µm. Although previous methodologies have been developed to reduce bubble size, most of these strategies involve manipulations of microbubbles post formation, such as gradient separation by gravitational forces or by physical filtration or floatation. While effective for selecting nanosized bubbles, these methods introduce potential for sample contamination, reduce bubble yield and stability, and waste stock materials in addition to being labor intensive. Additionally, the applicability of microbubbles as carriers (e.g., in cancer therapy) has been limited by a large size, which typically confines them to the vasculature.

SUMMARY

Embodiments described herein relate to prostate specific membrane antigen (PSMA) targeted nanobubbles for diagnostic and therapeutic applications. The PSMA targeted nanobubbles can be used as multifunctional and/or theranostic platforms for molecular imaging, drug therapy, gene therapy, chemotherapy, and anti-microbial applications. Each of the PSMA targeted nanobubbles can include a membrane that defines an internal void and at least one PSMA ligand coupled or linked to the membrane. The internal void can include at least one gas. The membrane of the nanobubble can include a hydrophilic outer domain at least partially defined by hydrophilic heads of at least one lipid and at least one nonionic triblock copolymer, and a hydrophobic inner domain at least partially defined by hydrophobic tails of the lipids. The at least one nonionic triblock copolymer can be effective to control the size of the nanobubble without compromising in vitro and in vivo echogenicity of the nanobubble. The PSMA targeted nanobubbles can have sizes such that upon intravenous administration to a subject are effective to enable the nanobubbles to extravasate from vasculature into parenchyma of the subject.

In other embodiments, the nonionic triblock copolymer can include at least one poloxamer. The poloxamer can have a molecular weight, for example, of about 1100 Daltons to about 3500 Daltons. The concentration of nonionic triblock copolymer in the lipid nanobubble can be about 0.06 mg/ml to about 1 mg/ml. The poloxamer:lipid molar ratio can be about 0.02 to about 0.5, for example, about 0.1 to about 0.3. The gas can have a low solubility in water and include, for example, a perfluorocarbon, such as perfluoropropane, hexafluoride, pefluoropentane, and perfluorobutane.

In some embodiments, the nanobubble can have a size that facilitates extravasation of the nanobubble from the vasculature into the parenchyma of the subject to allow the nanobubbles to be used in cancer therapy or diagnosis. For example, the nanobubble can have a diameter or size of about 30 nm to about 400 nm (or about 50 nm to about 300 nm, about 50 nm to about 200 nm, or about 50 nm to about 150 nm).

In other embodiments, the PSMA targeted nanobubbles can include an interpenetrating crosslinked biodegradable polymer that is non-covalently integrated into the hydrophobic domain of the nanobubble. The interpenetrating crosslinked biodegradable polymer can include, for example, a crosslinked acrylamide polymer, such as the reaction product of N, N-diethyl acrylamide (NNDEA) and N, N-bis(acryoyl) cystamine (BAC).

The interpenetrating crosslinked biodegradable polymer can stabilize the nanobubbles such that they can have a substantially smaller diameter (e.g., less than about 400 nm, 300 nm, 200 nm or less) and improved or enhanced retention of echogenic signal over 24 hours compared to similar sized nanobubbles that are not crosslinked. Moreover, in vivo analysis via ultrasound and fluorescence mediated tomography showed greater tumor extravasation and accumulation of the stabilized crosslinked nanobubbles compared to microbubbles.

In still other embodiments, the PSMA ligand can have the general formula (I):

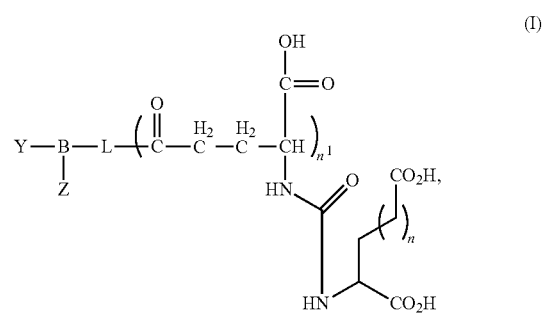

wherein:

n and $n^1$ are each independently 1, 2, 3, or 4;

L is an optionally substituted aliphatic or heteroaliphatic linking group;

B is a linking group, such as a peptide linking group, that includes at least one negatively charged amino acid; and Y is a lipid of the nanobubble membrane, which is directly or indirectly linked or coupled to B, and Z is hydrogen or at least one of a detectable moiety or label or a therapeutic agent that is directly or indirectly coupled to B.

In other embodiments, Z can be selected from the group consisting of an imaging agent, an anticancer agent, or a combination thereof. In still other embodiments, Z is a fluorescent label, such as Rhodamine, IRDye700, IRDye800, Cy3, Cy5, and/or Cy5.5

In other embodiments, the number of PSMA ligands linked to the membrane of a nanobubble can be at least about $1 \times 10^3$, $1 \times 10^4$, $2 \times 10^4$, $5 \times 10^4$, $1 \times 10^5$ or more.

In a still further aspect, the nanobubble can include at least one therapeutic agent that is contained within the membrane or conjugated to the membrane and/or contained polymer. The therapeutic agent can include at least one chemotherapeutic agent, anti-proliferative agent, biocidal agent, biostatic agent, or anti-microbial agent.

A further aspect of the application relates to a method for delineating PSMA expressing cancer cells in a region of interest (ROI) in a subject. The method can include administering to the subject a plurality of PSMA targeted nanobubbles. Each of the PSMA targeted nanobubbles can include a membrane that defines an internal void and at least one PSMA ligand coupled or linked to the membrane. The internal void can include at least one gas. The membrane of the nanobubble can include a hydrophilic outer domain at least partially defined by hydrophilic heads of at least one lipid and at least one nonionic triblock copolymer and a hydrophobic inner domain at least partially defined by hydrophobic tails of the lipids. The at least one nonionic triblock copolymer can be effective to control the size of the nanobubble without compromising in vitro and in vivo echogenicity of the nanobubble. The PSMA targeted nanobubbles can have sizes such that upon intravenous administration to a subject are effective to enable the nanobubbles to extravasate from vasculature into parenchyma of the subject After administering the PSMA targeted nanobubbles to the subject, at least one image of the region of interest (ROI) can be generated by ultrasound imaging the nanobubbles in the ROI to delineate cancer cells in the region of interest with a substantially enhanced effectiveness compared to clinically available microbubbles.

A further aspect of the application relates to a method for treating a neoplastic disorder in a subject. The method can include administering to neoplastic cells of the subject a composition comprising a plurality of PSMA targeted nanobubbles. Each of the PSMA targeted nanobubbles can include a membrane that defines an internal void and at least one PSMA ligand coupled or linked to the membrane. The internal void can include at least one gas. The membrane of the nanobubble can include a hydrophilic outer domain at least partially defined by hydrophilic heads of at least one lipid and at least one nonionic triblock copolymer and a hydrophobic inner domain at least partially defined by hydrophobic tails of the lipids. The at least one nonionic triblock copolymer can be effective to control the size of the nanobubble without compromising in vitro and in vivo echogenicity of the nanobubble. At least one chemotherapeutic can be contained in or coupled to the membrane or PSMA ligand.

Ultrasound can then be applied to a region of interest of the subject that includes the neoplastic cells and nanobubbles to cause release of the chemotherapeutic agent from the nanobubbles in the region of interest to the neoplastic cells.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1A:
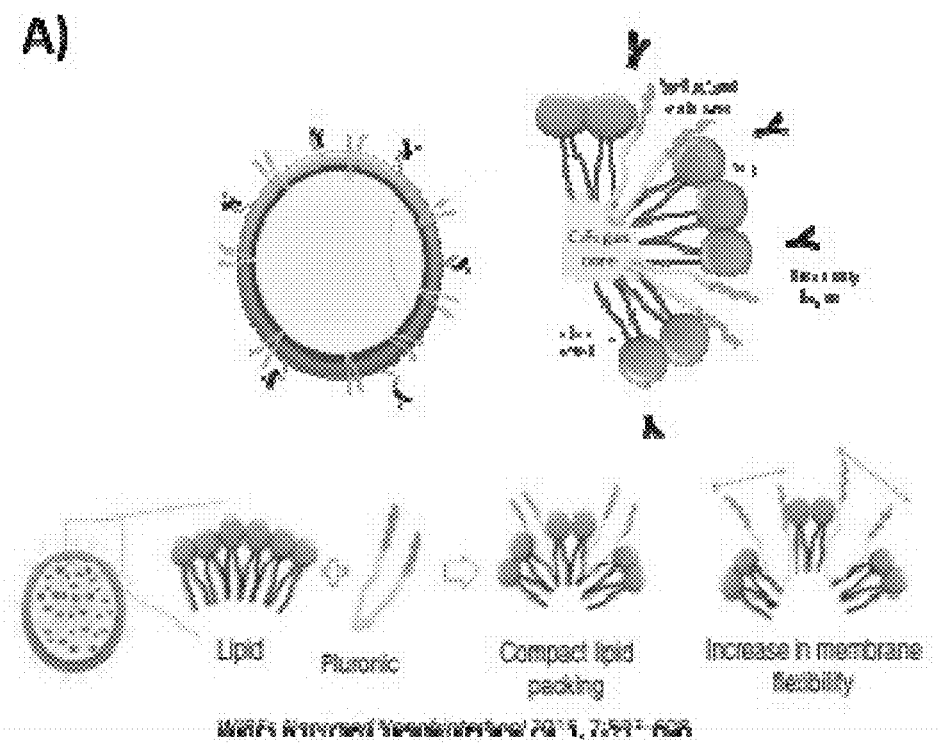
FIGS. 1(A-D) illustrate: (A) a nanobubble schematic, (B) a table showing average surface tension measurements of solutions with different Pluronic L10:lipids molar ratio, (C) plots showing nanobubble stability in ultrasound representative curves and half-life calculations for different pluronic L10:lipids molar ratio bubbles, and (D) ultrasound images of bubbles in vitro using custom-made agarose mold.

All scientific and technical terms used in this application have meanings commonly used in the art unless otherwise specified. The definitions provided herein are to facilitate understanding of certain terms used frequently herein and are not meant to limit the scope of the application.

As used herein, the term "neoplastic disorder" can refer to a disease state in a subject in which there are cells and/or tissues which proliferate abnormally. Neoplastic disorders can include, but are not limited to, cancers, sarcomas, tumors, leukemias, lymphomas, and the like.

As used herein, the term "neoplastic cell" can refer to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell." Non-limiting examples of cancer cells can include melanoma, breast cancer, ovarian cancer, prostate cancer, sarcoma, leukemic retinoblastoma, hepatoma, myeloma, glioma, mesothelioma, carcinoma, leukemia, lymphoma, Hodgkin lymphoma, Non-Hodgkin lymphoma, promyelocytic leukemia, lymphoblastoma, thymoma, lymphoma cells, melanoma cells, sarcoma cells, leukemia cells, retinoblastoma cells, hepatoma cells, myeloma cells, glioma cells, mesothelioma cells, and carcinoma cells.

As used herein, the term "tumor" can refer to an abnormal mass or population of cells that result from excessive cell division, whether malignant or benign, and all pre-cancerous and cancerous cells and tissues.

As used herein, the terms "treating" or "treatment" of a disease (e.g., a neoplastic disorder) can refer to executing a treatment protocol to eradicate at least one neoplastic cell. Thus, "treating" or "treatment" does not require complete eradication of neoplastic cells.

As used herein, the term "polymer" can refer to a molecule formed by the chemical union of two or more chemical units. The chemical units may be linked together by covalent linkages. The two or more combining units in a polymer can be all the same, in which case the polymer may be referred to as a homopolymer. The chemical units can also be different and, thus, a polymer may be a combination of the different units. Such polymers may be referred to as copolymers.

As used herein, the term "block copolymer" can refer to a polymer in which adjacent polymer segments or blocks are different, i.e., each block comprises a unit derived from a different characteristic species of monomer or has a different composition of units.

As used herein, the term "poloxamer" can refer to a series of non-ionic triblock copolymers comprised of ethylene oxide and propylene oxide. Poloxamers are synthesized by the sequential addition of propylene oxide, followed by ethylene oxide, to propylene glycol. The poly(oxyethylene) segment is hydrophilic and the poly(oxypropylene) segment is hydrophobic. The molecular weight of poloxamers may range from 1000 to greater than 16000. The basic structure of a poloxamer is HO—$(C_2H_4O)_a(C_3H_6O)_b(C_2H_4O)_a$—H, where "a" and "b" represent repeating units of ethylene oxide and propylene oxide, respectively.

As used herein, the term "poloxamine" can refer to a polyalkoxylated symmetrical block copolymer prepared from an ethylene diamine initiator. Poloxamines are synthesized using the same sequential order of addition of alkylene oxides as used to synthesize poloxamers. Structurally, the poloxamines include four alkylene oxide chains and two tertiary nitrogen atoms, at least one of which is capable of forming a quaternary salt. Poloxamines are also terminated by primary hydroxyl groups.

As used herein, the term "meroxapol" can refer to a symmetrical block copolymer consisting of a core of polyethylene glycol (PEG) polyoxypropylated to both its terminal hydroxyl groups, i.e., conforming to the general type $(PPG)_x$-$(PEG)_y$-$(PPG)_x$, wherein "x" and "y" represent repeating units of PPG and PEG, respectively, and being formed by an ethylene glycol initiator. As opposed to the poloxamers, which are terminated by two primary hydroxyl groups, meroxapols have secondary hydroxyl groups at the ends and the hydrophobe is split in two, each half on the outside of the surfactant.

"PSMA" refers to Prostate Specific Membrane Antigen, a potential carcinoma marker that has been hypothesized to serve as a target for imaging and cytotoxic treatment modalities for cancer.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment.

Embodiments described herein relate to PSMA targeted nanobubbles for diagnostic, therapeutic, and/or theranostic applications. The PSMA targeted nanobubbles can be used as multifunctional platforms for molecular imaging, drug therapy, gene therapy, chemotherapy, and/or anti-microbial applications. Nonionic triblock copolymers (e.g., poloxamers) when combined with lipids can form nanobubble contrast agents that can be coupled to PSMA targeting agents or ligands. The PSMA targeted nanobubbles can selectively recognize PSMA-expressing tumors, cancer cells, and/or cancer neovasculature in vivo and be used to deliver a therapeutic agent, detectable moiety, and/or theranostic agent to the PSMA-expressing tumors, cancer cells, and/or cancer neovasculature to treat and/or detect the PSMA-expressing tumors, cancer cells, and/or cancer neovasculature in a subject. The PSMA target nanobubbles when administered to a subject with cancer are clearly visible on ultrasound yet sufficiently small to move beyond leaky tumor vasculature, permitting greatly expanding molecular imaging capabilities of ultrasound at clinically relevant frequencies (e.g., 1 to 20 MHz).

The membranes of the nanobubbles described herein are tightly packed permitting a smaller size than traditionally formed microbubbles. Particle diameter has been the most widely accepted factor, which governs the resonant frequency of the bubble and its visibility with ultrasound. Typically, smaller bubbles vibrate faster, making them extremely difficult to detect with clinically relevant ultrasound frequencies. The nanobubbles described herein, however, are much more flexible than traditionally formed microbubbles as result of the nonionic triblock copolymer, which acts as a linker packed between lipids. This added flexibility of the nanobubbles reduces the resonant frequency or signal echogenicity to a point that make the nanobubbles detectable at frequencies as low as 1 MHz (e.g., 3.5 MHz) making the nanobubbles comparable to clinical agents but with the added benefit of small size.

In some embodiments, the PSMA targeted nanobubbles can include a membrane or shell that defines an internal void and at least one PSMA ligand coupled or conjugated to the membrane of the nanobubble. The internal void can include at least one gas. The membrane of the nanobubble can include a hydrophilic outer domain at least partially defined by hydrophilic heads of at least one lipid and at least one nonionic triblock copolymer, and a hydrophobic inner domain at least partially defined by hydrophobic tails of the lipids. The at least one nonionic triblock copolymer can be effective to control the size of the nanobubble without compromising in vitro and in vivo echogenicity of the nanobubble.

In some embodiments, the PSMA targeted nanobubbles can have an enhanced nanobubble stability compared to similar sized nanobubbles that are free of the nonionic triblock copolymer. "Nanobubble stability" can generally refer to the ability of the nanobubble to maintain its size in vitro and/or in vivo over time. For example, the nanobubble can maintain its size in vitro and/or in vivo over the course of minutes, days, weeks, or years. Additionally, nanobubble stability can refer to the polydispersity and/or zeta potential of the nanobubble. Polydispersity can refer to size distribution of the bubbles in solution, and zeta potential provides information on the stability of particle in suspension and is a function of particle surface charge. Nanobubbles described herein can have a polydispersity value of between about 0.1 and about 0.5, and a zeta potential of between about −30 mV and about −70 mV.

The nonionic triblock copolymers (e.g., poloxamers) can change the packing of the lipids in the nanobubble shell and allow the nanobubble size (diameter) to be tailored to as small as about 30 nm. In some embodiments, the nanobubble can have a size that facilitates extravasation of the nanobubble in cancer therapy or diagnosis. For example, the nanobubble can have a diameter or size of about 30 nm to about 400 nm (or about 50 nm to about 300 nm, about 50 nm to about 200 nm, or about 50 nm to about 150 nm), depending upon the particular nonionic triblock copolymer and the method used to form the nanobubble (described in greater detail below).

The at least one lipid used to form the membrane or shell can include any naturally-occurring, synthetic or semi-synthetic (i.e., modified natural) moiety that is generally amphipathic (i.e., including a hydrophilic component and a hydrophobic component). Examples of lipids can include fatty acids, neutral fats, phospholipids, oils, glycolipids, surfactants, aliphatic alcohols, waxes, terpenes and steroids. Semi-synthetic or modified natural lipids can include natural lipids that have been chemically modified in some fashion. The at least one lipid can be neutrally-charged, negatively-charged (i.e., anionic), or positively-charged (i.e., cationic). Examples of anionic lipids can include phosphatidic acid, phosphatidyl glycerol, and fatty acid esters thereof, amides of phosphatidyl ethanolamine, such as anandamides and methanandamides, phosphatidyl serine, phosphatidyl inositol and fatty acid esters thereof, cardiolipin, phosphatidyl ethylene glycol, acidic lysolipids, sulfolipids and sulfatides, free fatty acids, both saturated and unsaturated, and negatively-charged derivatives thereof. Examples of cationic lipids can include N-[1-(2,3-dioleoyloxy)propyl]-N,N,N-trimethyl-ammonium chloride and common natural lipids derivatized to contain one or more basic functional groups.

Other examples of lipids, any one or combination of which may be used to form the membrane, can include: phosphocholines, such as 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC), distearoylphosphatidylcholine (DSPC), and diarachidonylphosphatidylcholine (DAPC); phosphatidylethanolamines, such as dioleoylphosphatidylethanolamine, dipalmitoylphosphatidylethanolamine (DPPE), and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG); lipids bearing sulfonated mono-, di-, oligo- or polysaccharides; cholesterol, cholesterol sulfate, and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylaamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes, such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN (commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl)methylamino)octadecanoic acid; N-[12-(((7'-diethylaminocoumarin-3-yl)carbonyl)methylamino) octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoyl-glycerophosphoethanolamine and palmitoylhomocysteine; and/or any combinations thereof.

In some embodiments, the lipids can include a mixture of phospholipids having varying acyl chain lengths. For example, the lipids can include a mixture of at least two of DPPC, DBPC, DPPE, DSPE or DPPA. In one embodiment, the lipids can include a mixture of DPPC, DPPE, and DPPA at a ratio of, for example, about 4:1.4:1. In another embodiment, the lipids can include a mixture of DBPC, DPPE, and DPPA at a ratio of, for example, about 6:2:1. Advantageously, increasing the length of the acyl chain of the most predominant lipid in the mixture from 16 to 22 carbons (i.e., from DPPC to DBPC), while maintaining about the same molar ratios of all lipids in the formulation resulted in a fourfold improvement in half-life of the nanobubbles.

In some embodiments, the at least one nonionic triblock copolymer used to form the membrane can include an amphiphilic surfactant, such as a poloxamer, poloxamine, meroxapol, and/or combination thereof. In one example, the at least one nonionic triblock copolymer can comprise a poloxamer. The poloxamer can include any one or combination of a series of block copolymers of ethylene oxide and propylene oxide. The poly(oxyethylene) (PEO) and poly(oxypropylene) (PPO) segments may be hydrophilic and hydrophobic, respectively. The poloxamer may be a liquid, a paste, or a solid, and may have a molecular weight that ranges, for example, from about 1000 Daltons to about 3500 Daltons, although poloxamers having molecular weights greater or less than the these molecular weights can potentially be used. The concentration of nonionic triblock copolymer in the lipid nanobubble can be about 0.06 mg/ml to about 1 mg/ml.

The basic chemical formula of the poloxamer may be HO—$(C_2H_4O)_a(C_3H_6O)_b(C_2H_4O)_a$—H, where "a" and "b" represent repeating units of PEO and PPO, respectively. In some embodiments, "a" can be from 2 to 130 and "b" can be from 15 to 67. In one example, the poloxamer may have the chemical formula of HO—$(C_2H_4O)_2(C_3H_6O)_{31}(C_2H_4O)_2$—H. In another example of the present invention, the poloxamer may have the chemical formula of HO—$(C_2H_4O)_3(C_3H_6O)_{43}(C_2H_4O)_3$—H.

The poloxamer may be commercially available under various trade names including, for example, LUTROL, PLURONIC, SYNPERONIC (ICI), EMKALYX, PLURACARE, and PLURODAC. Examples of the PLURONIC series can include, but are not limited to, PLURONIC L10 (avg. $M_w$: 3200), PLURONIC L81 (avg. $M_w$: 2750), PLURONIC L61 (avg. $M_w$: 2000), PLURONIC L72 (avg. $M_w$: 2750), PLURONIC L62 (avg. $M_w$: 2500), PLURONIC L42 (avg. $M_w$: 1630), PLURONIC L63 (avg. $M_w$: 2650), PLURONIC L43 (avg. $M_w$: 1850), PLURONIC L64 (avg. $M_w$: 2900), PLURONIC L44 (avg. $M_w$: 2200), and PLURONIC L35 (avg. $M_w$: 1900). Other commercially available poloxamers can include compounds that are block copolymers of polyethylene and polypropylene glycol, such as SYNPERONIC L121, SYNPERONIC L122, SYNPERONIC P104, SYNPERONIC P105, SYNPERONIC P123, SYNPERONIC P85, SYNPERONIC P94, and compounds that are nonylphenyl polyethylene glycol, such as SYNPERONIC NP10, SYNPERONIC NP30 and SYNPERONIC NP5.

In another aspect of the application, the at least one nonionic triblock copolymer can comprise a poloxamine. The poloxamine can include a polyalkoxylated symmetrical block copolymer prepared from an ethylene diamine initiator. Poloxamines are synthesized using the same sequential order of addition of alkylene oxides as used to synthesize poloxamers. Structurally, the poloxamines can include four alkylene oxide chains and two tertiary nitrogen atoms, at least one of which is capable of forming a quaternary salt. Poloxamines can also be terminated by primary hydroxyl groups. Examples of poloxamines can include, but are not limited to, the TETRONIC and/or TETRONIC R series produced by BASF. For example, poloxamines can include TETRONIC 904, TETRONIC 908, TETRONIC 1107, TETRONIC 90R4, TETRONIC 1304, TETRONIC 1307 and TETRONIC T1501.

In another aspect of the application, the at least one nonionic triblock copolymer can include a meroxapol. Meroxapols can include a symmetrical block copolymer consisting of a core of PEG polyoxypropylated to both its terminal hydroxyl groups, i.e., conforming to the general type $(PPG)_x$-$(PEG)_y$-$(PPG)_x$, and being formed by an ethylene glycol initiator. Examples of meroxapols can include, but are not limited to, MEROXAPOL 105, MEROXAPOL 108, MEROXAPOL 172, MEROXAPOL 174, MEROXAPOL 252, MEROXAPOL 254, MEROXAPOL 258 and MEROXAPOL 311.

In other embodiments, the PSMA targeted nanobubbles can include an interpenetrating crosslinked biodegradable polymer that is non-covalently integrated into the hydrophobic domain of the nanobubble. The interpenetrating crosslinked biodegradable polymer can stabilize the nanobubbles such that they can have a substantially smaller diameter (e.g., less than about 400 nm, 300 nm, 200 nm or less) and improved or enhanced retention of echogenic signal over 24 hours compared to similar stabilized nanobubbles that are not crosslinked. Moreover, in vivo analysis via ultrasound and fluorescence mediated tomography showed greater tumor extravasation and accumulation of the stabilized crosslinked nanobubbles compared to microbubbles.

In some embodiments, the interpenetrating cross-linking biodegradable polymer can include an acrylamide, such as N, N-diethyl acrylamide (NNDEA), that is reacted with or crosslinked with a bifunctional crosslinker, such as N, N-bis(acryoyl)cystamine (BAC), in the presence of an initiator, such as a radical photoinitiator (e.g., IRGACURE 2959). Incorporation of cross-linking agents into the nanobubble membrane was found to increase the stability of pluronic polymeric micelles below their critical micelle concentration (CMC). In these nanobubbles, the hydrophobic network is non-covalently integrated into the inner ring or the hydrophobic domain of the nanobubble to improve structural stability while retaining membrane flexibility and reduce diffusion of hydrophobic gas from the core.

In some embodiments, the acrylamide monomer can include at least one of N-(n-octadecyl)acrylamide, acrylamide, N-benzylmethacrylamide, N,N-diethylacrylamide, N,N-dimethylacrylamide, N,N-dimethylmethacrylamide, N,N-diphenyl methacrylamide, N(n-dodecyl)methacrylamide, N-(tert-octyl)acrylamide, N-iso-propylacrylamide, N-[2-N,N-Dimethylamino)-ethyl]methacrylamide, N-[3-(N, N-Dimethylamino)-propyl] acrylamide, or [3-(N,N-Dimethylamino)-propyl] methacrylamide, N-tert-butylacrylamide, N-(butoxymethyl)acrylamide, diacetoneacrylamide, dodecylacrylamide, ethylenebisacrylamide, n-(hydroxymethyl)acrylamide, methylenebisacrylamide, phenylacrylamide, or combinations thereof. The particular acrylamide monomer selected or combination of acrylamide monomers can affect the stability of the nanobubbles. More hydrophic acrylamide monomers can form more hydrophic acylamide polymers that can enhance stability of the nanobubbles compared to less hydrophobic acrylamide monomers and polymers.

The membrane defining the nanobubble can be concentric or otherwise and have a unilamellar configuration (i.e., comprised of one monolayer or bilayer), an oligolamellar configuration (i.e., comprised of about two or about three monolayers or bilayers), or a multilamellar configuration (i.e., comprised of more than about three monolayers or bilayers). The membrane can be substantially solid (uniform), porous, or semi-porous.

The internal void defined by the membrane can include at least one gas. The gas can have a low solubility in water and be, for example, a perfluorocarbon, such as perfluoropropane (e.g., octafluoropropane), hexafluoride, pefluoropentane, and perfluorobutane.

The membrane also includes at least one PSMA targeting moiety or PSMA ligand that can selectively recognize PSMA-expressing tumors, cancer cells, and/or cancer neovasculature in vivo. PSMA is a transmembrane protein that is highly overexpressed (100-1000 fold) on almost all prostate cancer (PC) tumors. Only 5-10% of primary PC lesions have been shown to be PSMA-negative. PSMA expression levels increase with higher tumor stage and grade.

Small molecule PSMA ligands bind to the active site in the extracellular domain of PSMA and are internalized and endosomally recycled, leading to enhanced tumor uptake and retention and high image quality. Examples of PSMA ligands are described in Afshar-Oromieh A, Malcher A, Eder M, et al. PET imaging with a [68Ga]gallium-labelled PSMA ligand for the diagnosis of prostate cancer: biodistribution in humans and first evaluation of tumour; Weineisen M, Schottelius M, Simecek J, et al. 68Ga- and 177Lu-Labeled PSMA I&T: Optimization of a PSMA-Targeted Theranostic Concept and First Proof-of-Concept Human Studies. *J Nucl Med.* 2015; 56:1169-1176. lesions. *Eur J Nucl Med Mol Imaging.* 2013; 40:486-495; Cho S Y, Gage K L, Mease R C, et al. Biodistribution, tumor detection, and radiation dosimetry of 18F-DCFBC, a low-molecular-weight inhibitor of prostate-specific membrane antigen, in patients with metastatic prostate cancer. *J Nucl Med.* 2012; 53:1883-1891; and Rowe S P, Gage K L, Faraj S F, et al. (1)(8)F-DCFBC PET/CT for PSMA-Based Detection and Characterization of Primary Prostate Cancer. *J Nucl Med.* 2015; 56:1003-1010.

Other examples of PSMA ligands are described in U.S. Pat. Nos. 6,875,886, 6,933,114, and 8,609,142, which are incorporated herein by reference in their entirety.

In some embodiments, the PSMA ligand can have the general formula (I):

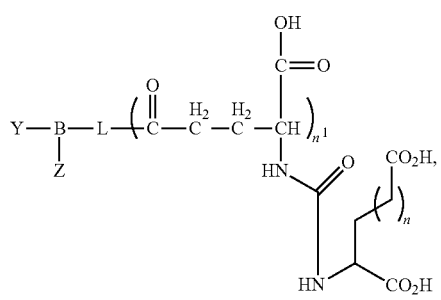

wherein:
n and $n^1$ are each independently 1, 2, 3, or 4;
L is an optionally substituted aliphatic or heteroaliphatic linking group;
B is linker, such as a peptide linker, that includes at least one negatively charged amino acid; and
Y is a lipid of the nanobubble membrane, which is directly or indirectly linked or coupled to B, and
Z is hydrogen or at least one of a detectable moiety or label or a therapeutic agent, which is directly or indirectly linked or coupled to B. In other embodiments, Z can be selected from the group consisting of an imaging agent, an anticancer agent, or a combination thereof. In still other embodiments, Z is a fluorescent label, such as Rhodamine, IRDye700, IRDye800, Cy3, Cy5, and/or Cy5.5.

In other embodiments, L can be an optionally substituted aliphatic or heteroaliphatic group that includes at least one ring selected from the group consisting of an optionally substituted 4 to 7 membered nonaromatic heterocyclic ring and an optionally substituted C4-C7 cycloalkyl ring.

An aliphatic group is a straight chained, branched or cyclic non-aromatic hydrocarbon, which is completely saturated or which contains one or more units of unsaturation. An alkyl group is a saturated aliphatic group. Typically, a straight chained or branched aliphatic group has from 1 to about 10 carbon atoms, preferably from 1 to about 4, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. C1-C4 straight chained or branched alkyl or alkoxy groups or a C3-C8 cyclic alkyl or alkoxy group (preferably C1-C4 straight chained or branched alkyl or alkoxy group) are also referred to as a "lower alkyl" or "lower alkoxy" groups; such groups substituted with —F, —Cl, —Br, or —I are "lower haloalkyl" or "lower haloalkoxy" groups; a "lower hydroxyalkyl" is a lower alkyl substituted with —OH; and the like.

Suitable optional substituents for a substitutable atom in alkyl, cycloalkyl, aliphatic, cycloaliphatic, heterocyclic, benzylic, aryl, or heteroaryl groups described herein are those substituents that do not substantially interfere with the activity of the disclosed compounds. A "substitutable atom" is an atom that has one or more valences or charges available to form one or more corresponding covalent or ionic bonds with a substituent. For example, a carbon atom with one valence available (e.g., —C(—H)=) can form a single bond to an alkyl group (e.g., —C(-alkyl)=), a carbon atom with two valences available (e.g., —C(H$_2$)—) can form one or two single bonds to one or two substituents (e.g., —C(alkyl)(Br))—, —C(alkyl)(H)—) or a double bond to one substituent (e.g., —C=O)—), and the like. Substitutions contemplated herein include only those substitutions that form stable compounds.

For example, suitable optional substituents for substitutable carbon atoms include —F, —Cl, —Br, —I, —CN, —NO$_2$, —OR$^a$, —C(O)R$^a$, —OC(O)R$^a$, —C(O)OR$^a$, —SR$^a$, —C(S)R$^a$, —OC(S)R$^a$, —C(S)OR$^a$, —C(O)SR$^a$, —C(S)SR$^a$, —S(O)R$^a$, —SO$_2$R$^a$, —SO$_3$R$^a$, —POR$^a$R$^b$, PO$_2$R$^a$R$_b$, —PO$_3$R$^a$R$^b$, —PO$_4$R$^a$R$^b$, —P(S)R$^a$R$^b$, —P(S)OR$^a$R$^b$, —P(S)O$_2$R$^a$R$^b$, —P(S)O$_3$R$^a$R$^b$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N (R$^a$R$^b$), —NR$^c$C(O)R$^a$, —NR$^c$C(O)OR$^a$, —NR$^c$C(O)N (R$^a$R$^b$), —C(NR$^c$)—N(R$^a$R$^b$), —NR$^d$—C(NR$^c$)—N(R$^a$R$^b$), —NR$^a$N(R$^a$R$^b$), —CRC=CR$^a$R$^b$, —C=CR$^a$, =O, =S, =CR$^a$R$^b$, =NR$^a$, =NOR$^a$, =NNR$^a$, optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl, wherein R$^a$-R$^d$ are each independently —H or an optionally substituted aliphatic, optionally substituted cycloaliphatic, optionally substituted heterocyclic, optionally substituted benzyl, optionally substituted aryl, or optionally substituted heteroaryl, or, —N(R$^a$R$^b$), taken together, is an optionally substituted heterocyclic group. Also contemplated are isomers of these groups.

Suitable substituents for nitrogen atoms having two covalent bonds to other atoms include, for example, optionally substituted alkyl, optionally substituted cycloalkyl, optionally substituted aliphatic, optionally substituted cycloaliphatic, optionally substituted heterocyclic, optionally substituted benzyl, optionally substituted aryl, optionally substituted heteroaryl, —CN, —NO$_2$, —OR$^a$, —C(O)R$^a$, —OC(O)R$^a$, —C(O)OR$^a$, —SR$^a$, —S(O)R$^a$, —SO$_2$R$^a$, —SO$_3$R$^a$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), and the like.

Suitable substituents for nitrogen atoms having three covalent bonds to other atoms include —OH, alkyl, and alkoxy (preferably C1-C4 alkyl and alkoxy). Substituted ring nitrogen atoms that have three covalent bonds to other ring atoms are positively charged, which is balanced by counteranions such as chloride, bromide, fluoride, iodide, formate, acetate and the like. Examples of other suitable counter anions are provided in the section below directed to suitable pharmacologically acceptable salts.

In other embodiments, B can include at least one, two, three, four, or more negatively charged amino acids, i.e., amino acids with a negative charged side chain, such as glutamic acid, aspartic acid, and/or tyrosine. B can also include other amino acids that facilitate binding of B to Y and/or the PSMA ligand to Z.

In some embodiments, B can have the following formula:

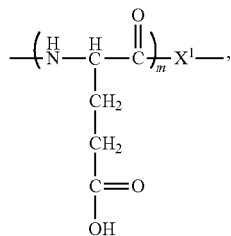

wherein m is 1, 2, 3, or 4, and X$^1$ is an amino acid, which is directly or indirectly linked to least one of an amino acid, peptide, detectable moiety, therapeutic agent, theranostic agent, and/or nanobubble membrane lipid.

In certain embodiments, X$^1$ can facilitate binding of B to Y and/or the PSMA ligand to a detectable moiety, therapeutic agent, and/or theranostic agent.

In other embodiments, the PSMA ligand can have the general formula:

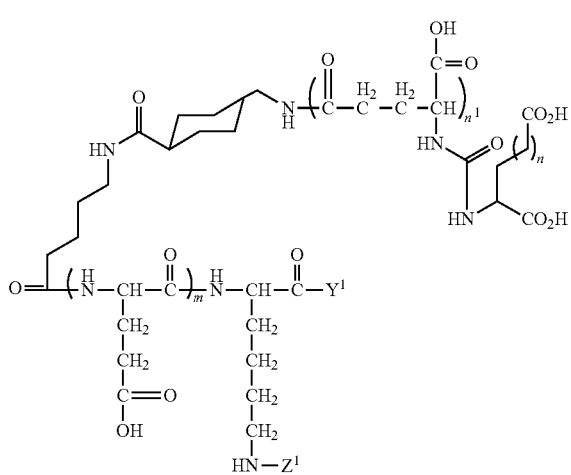

wherein m, n, and n$^1$ are each independently 1, 2, 3, or 4,
Y$^1$ includes a lipid of the nanobubble membrane, which is directly or indirectly coupled or linked to the PSMA ligand,
and Z$^1$ is a H or can include at least one of an amino acid, peptide, detectable moiety or label, therapeutic agent, or theranostic agent.

In other embodiments, the PSMA ligand can have the formula:

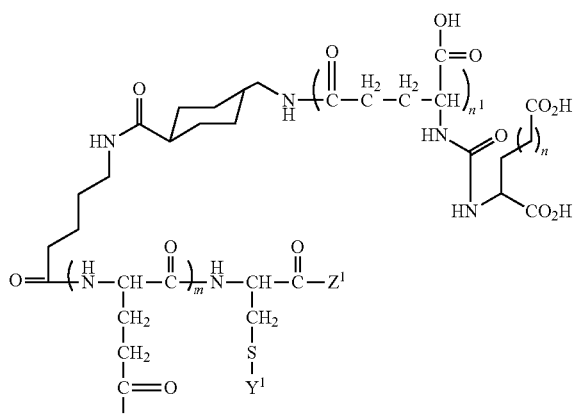

wherein m, n, and n$^1$ are each independently 1, 2, 3, or 4,
Y$^1$ includes a lipid of the nanobubble membrane, which is directly or indirectly coupled or linked to the PSMA ligand,
and Z$^1$ is a H or can include at least one of an amino acid, peptide, detectable moiety or label, therapeutic agent, or theranostic agent.

In some embodiments, Z and Z$^1$ can include a detectable moiety or label that is directly or indirectly coupled to B or the PSMA ligand. Examples of detectable moieties include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, chelating groups, and biotin, dioxigenin or other haptens and proteins for which antisera or monoclonal antibodies are available.

In some embodiments, radionuclides can include atomic isotopes such as $^{99m}$Tc, $^{111}$In, $^{123}$I, $^{124}$I, $^{131}$I, $^{67}$Ga, $^{201}$Tl, $^{125}$I, $^{18}$F, $^{11}$C, $^{76}$Br, $^{124}$I, $^{68}$Ga, $^{82}$Rb, $^{13}$N, $^{64}$Cu, $^{90}$Y, $^{188}$Rh, T(tritium), $^{32}$P, $^{35}$S, $^{153}$Sm, $^{89}$Sr, $^{211}$At, and $^{89}$Zr. These isotopes can be directly or indirectly coupled to the PSMA ligand.

Fluorescence labeling agents or infrared labeling agents include those known to the art, many of which are commonly commercially available, such as ALEXA 350, PACIFIC BLUE, MARINA BLUE, ACRIDINE, EDANS, COUMARIN, BODIPY 493/503, CY2, BODIPY FL-X, DANSYL, ALEXA 488, FAM, OREGON GREEN, RHODAMINE GREEN-X, TET, ALEXA 430, CAL GOLD, BODIPY R6G-X, JOE, ALEXA 532, VIC, HEX, CAL ORANGE™, ALEXA 555, BODIPY 564/570, BODIPY TMR-X, QUASAR™ 570, ALEXA 546, TAMRA, RHODAMINE RED-X, BODIPY 581/591, CY3.5, CY5.5, ROX, ALEXA 568, CAL RED, BODIPY TR-X, ALEXA 594, BODIPY 630/650-X, PULSAR 650, BODIPY 630/665-X, ALEXA 647, IR700, IR800, and QUASAR 670. Fluorescence labeling agents can include other known fluorophores, or proteins known to the art, for example, green fluorescent protein. The fluorescence labeling agents can be directly or indirectly coupled to the PSMA ligands, administered to a subject or a sample, and the subject/sample examined by fluorescence spectroscopy or imaging to detect the labeled compound.

Chelating groups (with or without a chelated metal group) can include those disclosed in U.S. Pat. No. 7,351,401, which is herein incorporated by reference in its entirety.

Near infrared imaging groups are disclosed in, for example, Tetrahedron Letters 49(2008) 3395-3399; Angew. Chem. Int. Ed. 2007, 46, 8998-9001; Anal. Chem. 2000, 72, 5907; Nature Biotechnology vol 23, 577-583; Eur Radiol (2003) 13: 195-208; and Cancer 67: 1991 2529-2537, which are herein incorporated by reference in their entirety.

Quantum dots, e.g., semiconductor particles, can be employed as described in Gao, et al "In vivo cancer targeting and imaging with semiconductor quantum dots", Nature Biotechnology, 22, (8), 2004, 969-976, the entire teachings of which are incorporated herein by reference. The PSMA ligands described herein can be coupled to the quantum dots, administered to a subject or a sample, and the subject/sample examined by spectroscopy or imaging to detect the labeled compound.

Magnetic resonance imaging (MRI) contrast agents, can include positive contrast agents and negative contrast agents. The PSMA ligands described herein can be coupled to the MRI agents, administered to a subject or a sample, and the subject/sample examined by MRI or imaging to detect the labeled compound. Positive contrast agents (typically appearing predominantly bright on MRI) can include typically small molecular weight organic compounds that chelate or contain an active element having unpaired outer shell electron spins, e.g., gadolinium, manganese, iro, or the like. Typical contrast agents include gadopentetate dimeglumine, gadoteridol, gadoterate meglumine, mangafodipir trisodium, gadodiamide, and others known to the art. Negative contrast agents (typically appearing predominantly dark on MRI) can include small particulate aggregates comprised of superparamagnetic materials, for example, particles of superparamagnetic iron oxide (SPIO). Negative contrast agents can also include compounds that lack the hydrogen atoms associated with the signal in MRI imaging, for example, perfluorocarbons (perfluorochemicals).

In some embodiments, a PSMA ligand that is coupled to a fluorescence label agent, infrared label, or therapeutic agent can have the following formula:

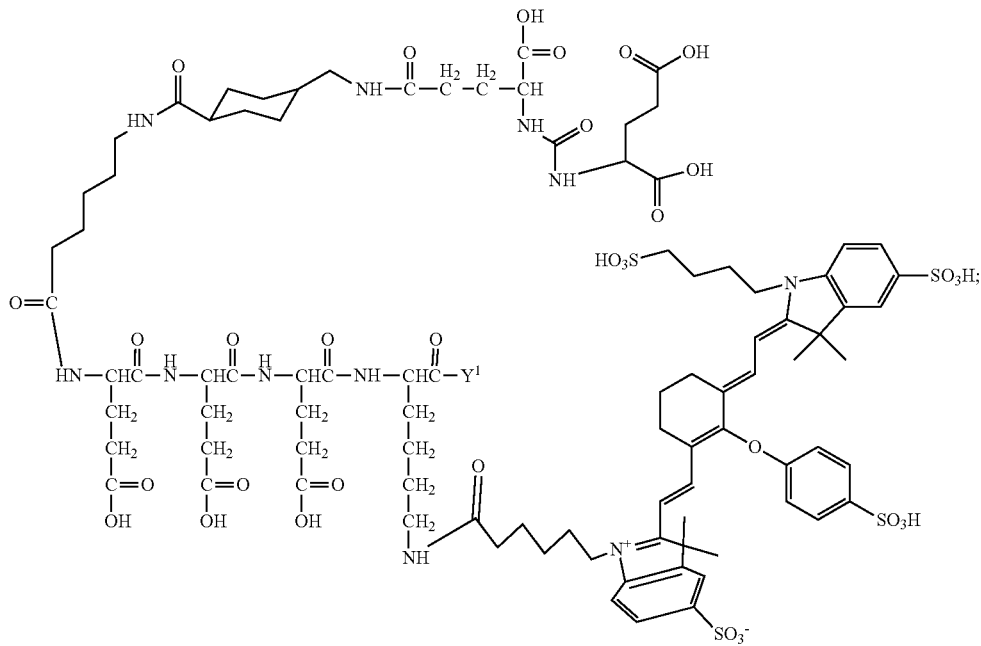

-continued
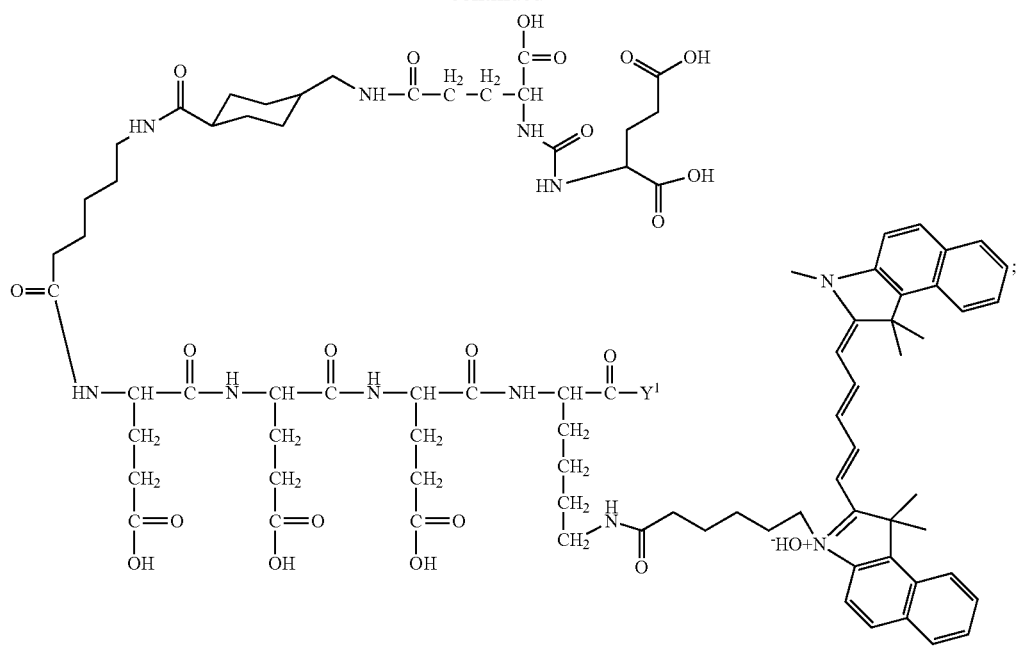
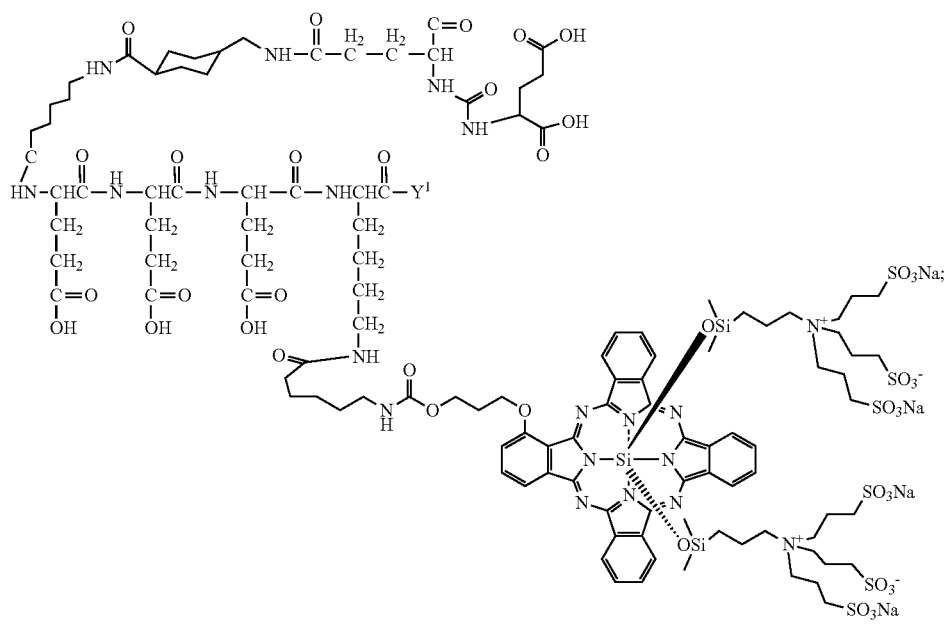

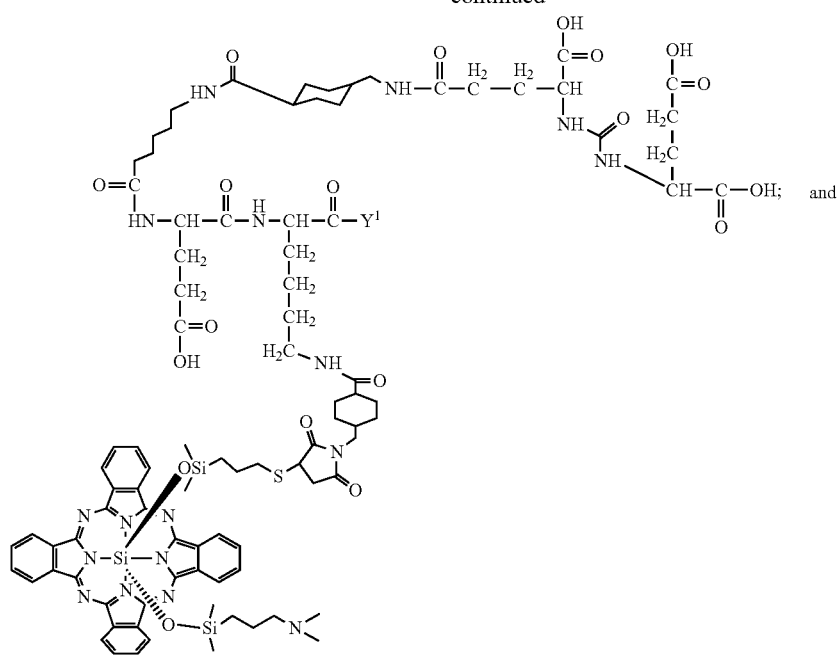
and
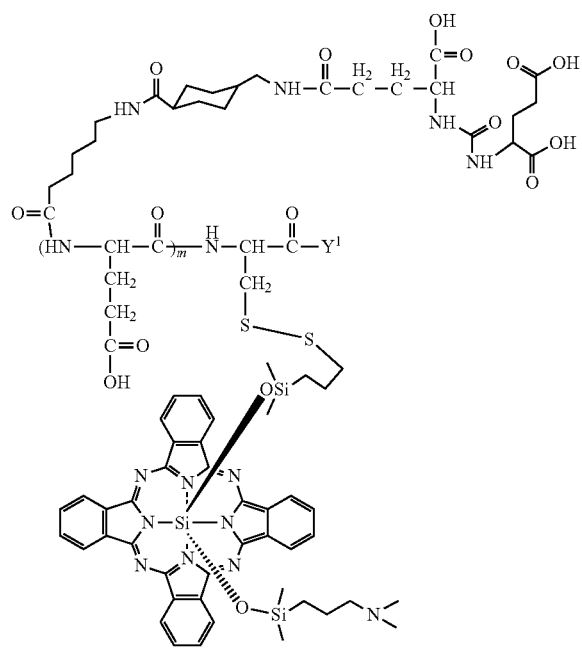

wherein $Y^1$ includes a lipid of the nanobubble membrane that is directly or indirectly coupled or linked to the PSMA ligand.

In other embodiments, a PSMA ligand that is coupled to a radiolabel can have the following formula.

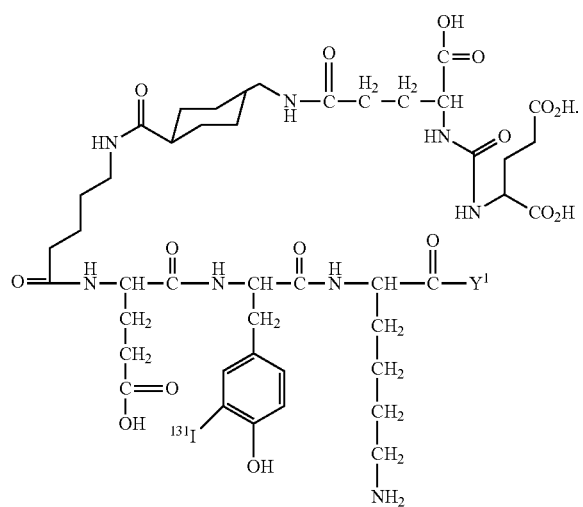

wherein $Y^1$ includes a lipid of the nanobubble membrane that is directly or indirectly coupled or linked to the PSMA ligand.

The number of PSMA ligands coupled or linked to the membrane of a nanobubble can be at least about $1\times10^3$, $1\times10^4$, $2\times10^4$, $5\times10^4$, $1\times10^5$ or more. The term "coupled" or "linked" when made in reference to the PSMA ligand and the lipid of the nanobubble membrane as used herein means covalently linking the PSMA ligand to a lipid of the nanobubble membrane subject to the limitation that the nature and size of the PSMA ligand and the site at which it is covalently linked to the lipid of the nanobubble membrane does not interfere with the binding of the PSMA ligand to cancer cells.

PSMA ligands optionally including a detectable moiety, therapeutic agent, theranostic agent can be coupled to a lipid of the nanobubble membrane either directly or indirectly (e.g., via a binder group). In some embodiments, the PSMA ligand is directly attached to a functional group capable of reacting with a functional group of the lipid. For example, the PSMA ligand can include lysines that can be capable of reacting with a carbonyl-containing group, such as an anhydride or an acid halide, or with an alkyl group containing a good leaving group (e.g., a halide). The PSMA ligand can also include cysteines that facilitate chemical coupling via thiol-selective chemistry (e.g., maleimide-activated compounds). Further, the PSMA ligands can include tyrosines, which can be modified using diazonium coupling reactions.

In other embodiments, a chemical binder group can be used. A binder group can serve to increase the chemical reactivity of a substituent on either the PSMA ligand and/or nanobubble, and thus increase the coupling efficiency. Binder chemistries can include maleimidyl binders, which can be used to bind to thiol groups, isothiocyanate and succinimidyl (e.g., N-hydroxysuccinimidyl (NHS)) binders, which can bind to free amine groups, diazonium which can be used to bind to phenol, and amines, which can be used to bind with free acids such as carboxylate groups using carbodiimide activation.

Useful functional groups are present on the PSMA ligands based on the particular amino acids present, and additional groups can be designed. It will be evident to those skilled in the art that a variety of bifunctional or polyfunctional reagents, both homo- and hetero-functional (such as those described in the catalog of the Pierce Chemical Co., Rockford, Ill.), can be employed as a binder group. Coupling can be affected, for example, through amino groups, carboxyl groups, sulfhydryl groups or oxidized carbohydrate residues.

Other types of binding chemistries are also available. For example, methods for conjugating polysaccharides to peptides are exemplified by, but not limited to coupling via alpha- or epsilon-amino groups to NaIO$_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide binder wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

In some embodiments, the lipids of the nanobubble membrane can be modified to include a linker to link the PSMA targeting agent and/or a detectable moiety and/or therapeutic agent to the membrane of the nanobubble. The linker can be of any suitable length and contain any suitable number of atoms and/or subunits. The linker can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

The PSMA targeted nanobubbles can also include other materials, such as liquids, oils, bioactive agents, diagnostic agents, and/or therapeutic agents. The materials can be encapsulated by the membrane and/or linked or conjugated to the membrane.

Bioactive agents encapsulated by and/or linked to the membrane can include any substance capable of exerting a biological effect in vitro and/or in vivo. Examples of bioactive agents can include, but are not limited to, chemotherapeutic agents, biologically active ligands, small molecules, DNA fragments, DNA plasmids, interfering RNA molecules, such as siRNAs, oligonucleotides, and DNA encoding for shRNA. Diagnostic agents can include any substance that may be used for imaging a region of interest (ROI) in a subject and/or diagnosing the presence or absence of a disease or diseased tissue in a subject. Therapeutic agents can refer to any therapeutic or prophylactic agent used in the treatment (including the prevention, diagnosis, alleviation, or cure) of a malady, affliction, condition, disease or injury in a subject. It will be appreciated that the membrane can additionally or optionally include proteins, carbohydrates, polymers, surfactants, and/or other membrane stabilizing materials, any one or combination of which may be natural, synthetic, or semi-synthetic.

In some embodiments, the bioactive agent can include a therapeutic agent, such as a chemotherapeutic agent, an anti-proliferative agent, an anti-microbial agent, a biocidal agent, and/or a biostatic agent. The therapeutic agent can be encapsulated by and/or linked to the membrane of the nanobubble.

The PSMA targeted nanobubbles described herein can be administered to the subject by, for example, systemic, topical, and/or parenteral methods of administration. These methods include, e.g., injection, infusion, deposition, implantation, or topical administration, or any other method of administration where access to the tissue is desired. In one example, administration can be by intravenous injection in the subject. Single or multiple administrations of the PSMA targeted nanobubbles can be given. "Administered", as used herein, means provision or delivery is in an amount(s) and for a period of time(s) effective to label cancer cells in the subject.

The PSMA targeted nanobubbles described herein can be administered to a subject in a detectable quantity or imaging effective quantity of a pharmaceutical composition containing the PSMA ligands. A "detectable quantity" means that the amount of the detectable PSMA targeted nanobubbles that is administered is sufficient to enable detection of binding of the PSMA targeted nanobubbles to the cancer cells. An "imaging effective quantity" means that the amount of the detectable PSMA targeted nanobubbles that is administered is sufficient to enable imaging of binding of the PSMA targeted nanobubbles to the cancer cells. By way of example, where the subject is a human at least about $1\times10^{10}$, $1\times10^{11}$, $1\times10^{12}$, $1\times10^{13}$, $1\times10^{14}$ or more PSMA targeted nanobubbles can be intravenously administered to a subject to detect, image, or delineate cancer cells in a subject.

The PSMA targeted nanobubbles described herein administered to a subject can be used to determine the presence, location, and/or distribution of cancer cells, i.e., PSMA expressing cancer cells or PSMA expressing neovaculature of the cancer cells, in an organ or body area of a patient. The presence, location, and/or distribution of the PSMA ligands coupled to a detectable moiety in the animal's tissue, e.g., brain tissue, can be visualized (e.g., with an in vivo imaging modality described above). "Distribution" as used herein is the spatial property of being scattered about over an area or volume. In this case, "the distribution of cancer cells" is the spatial property of cancer cells being scattered about over an area or volume included in the animal's tissue, e.g., prostate tissue. The distribution of the PSMA targeted nanobubbles may then be correlated with the presence or absence of cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject.

In one aspect, the PSMA targeted nanobubbles described herein may be administered to a subject to assess the distribution of prostate cancer cells in a subject and correlate the distribution to a specific location. Surgeons routinely use stereotactic techniques and intra-operative MRI (iMRI) in surgical resections. This allows them to specifically identify and sample tissue from distinct regions of the tumor such as the tumor edge or tumor center. Frequently, they also sample regions of prostate on the tumor margin that are outside the tumor edge that appear to be grossly normal but are infiltrated by dispersing tumor cells upon histological examination.

The PSMA targeted nanobubbles described herein can be used in intra-operative imaging techniques to guide surgical resection and eliminate the "educated guess" of the location of the tumor by the surgeon. Previous studies have determined that more extensive surgical resection improves patient survival. Thus, the PSMA ligands coupled to the nanobubbles described herein that function as diagnostic molecular imaging agents have the potential to increase patient survival rates.

In other embodiments, the PSMA targeted nanobubbles can be formulated such that the internal void of at least one of the nanobubbles includes at least one contrast agent, such as octafluoropropane. Examples of contrast agents (besides octafluoropropane) that may be incorporated into the nanobubbles are known in the art and can include stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules.

The following examples are for the purpose of illustration only and is not intended to limit the scope of the claims, which are appended hereto.

Example 1

Effect of the Surfactant Pluronic on the Stability of Lipid-Stabilized Perfluorocarbon Nanobubbles Due to their 1-10 µm size range, microbubbles (MBs) have limited use in cancer detection and treatment. To expand contrast enhanced US capabilities, we have developed sub-micron contrast agents via the addition of Pluronic, a nonionic triblock copolymer surfactant, to the phospholipid shell stabilizing perfluoropropane ($C_3F_8$) gas (FIG. 1A). Nanobubbles (NBs), with diameter of about 200 nm, can take advantage of the EPR effect, extravasate the leaky tumor vasculature and accumulate in tumors. Prior work has shown that bubble echogenicity and stability are, in part, dependent on the surface tension of the stabilizing shell. In this example, we evaluated the effect of Pluronic on surface tension of lipid films and how its presence in the NB shell affects echogenicity and signal decay at clinically-relevant imaging frequencies.

Methods

Pluronic L10 (MW 3200, PPO/PEO units of 49.7/7.3), at three Pluronic:lipid molar ratios (0.02, 0.2, and 0.4), was incorporated into the lipid film composed of a mixture of DPPC, DPPE, DPPA and DSPE-PEG. Bubble diameter was measured with dynamic light scattering (DLS). The surface tension of each composition was measured using pendant drop tensiometry. To test the effect of Pluronic concentration on bubble stability, NBs with the same Pluronic:lipid ratios were formulated by hydrating the lipid mixture described above with the appropriate Pluronic concentration and exchanging air with $C_3F_8$. Bubbles were then activated using mechanical agitation and imaged in PBS inside an agarose phantom using a standard diagnostic US scanner (Toshiba Aplio) in contrast harmonic mode at 12 MHz, MI 0.1, and 0.2 frames per second.

Results

Figure 1B:
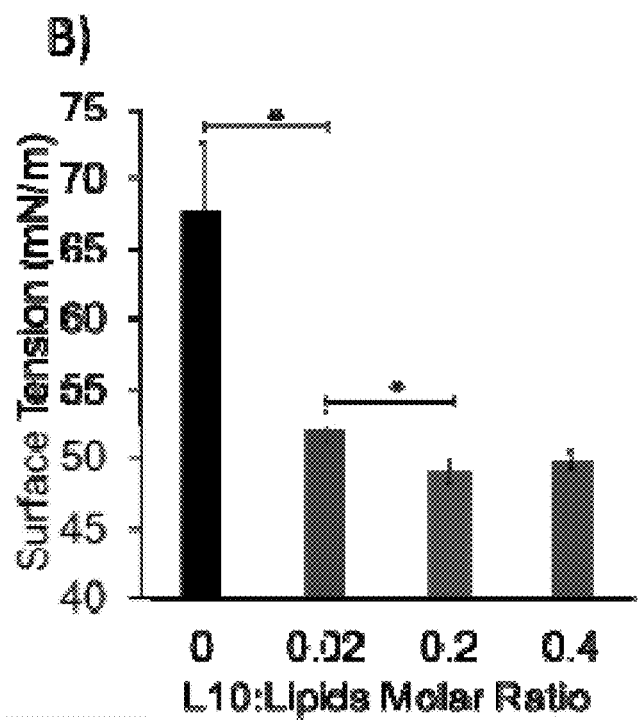
Figure 1C:
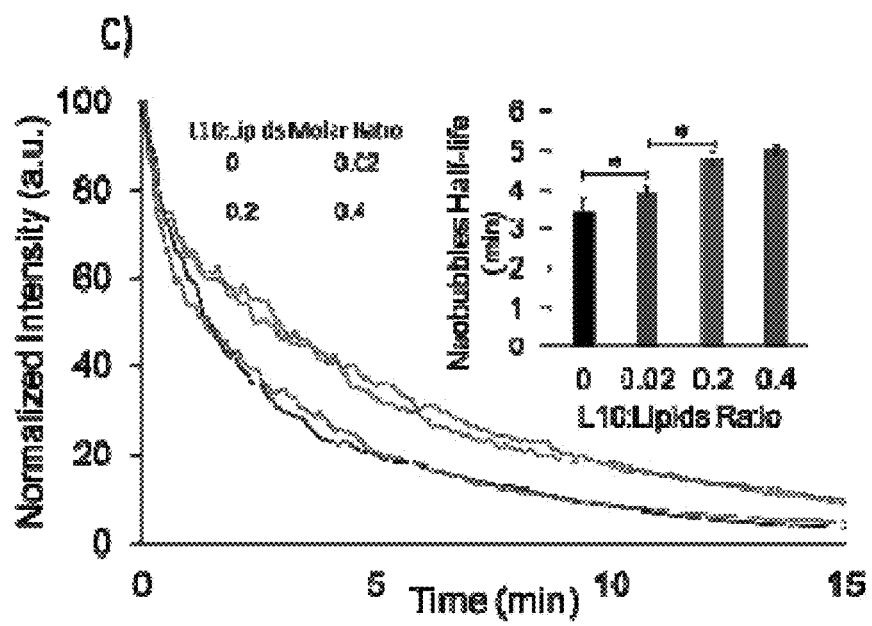
Figure 1D:
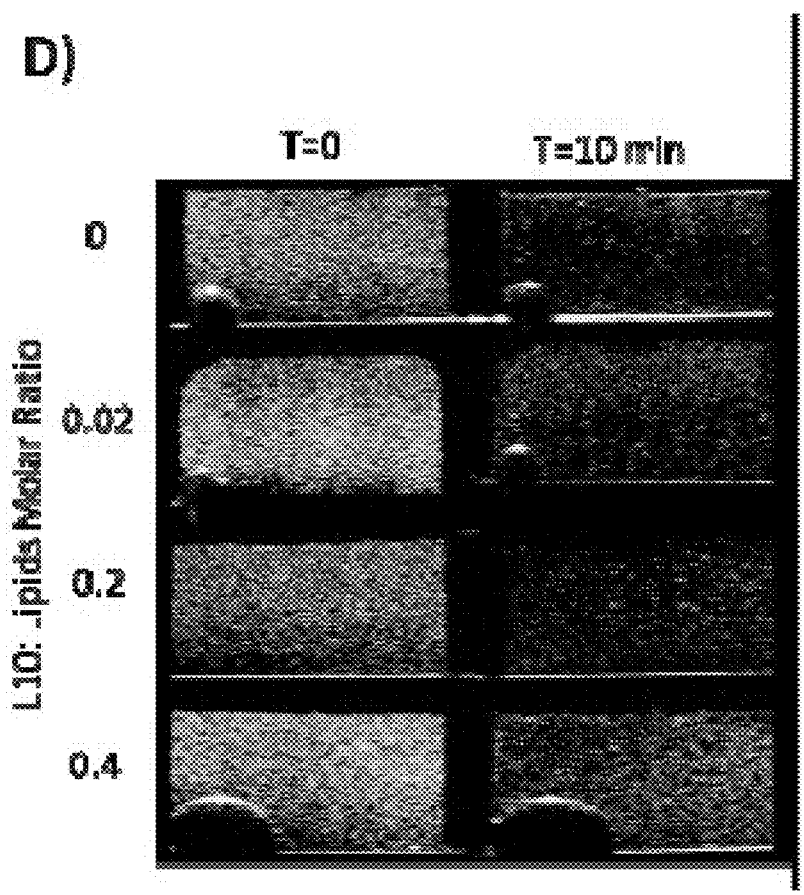
Figure 2A:
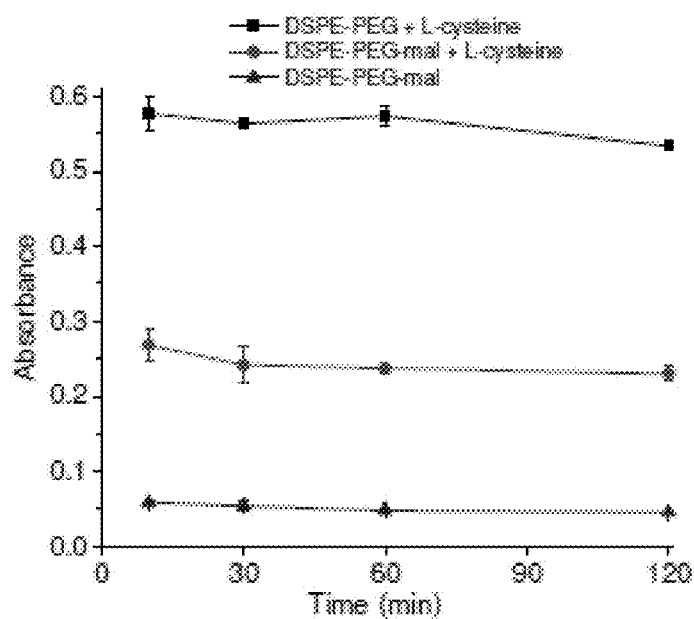
FIGS. 2(A-B) illustrate graphs showing efficiency of PSMA-1-cys peptide synthesis and lipid via maleimide-thiol binding.

The incorporation of Pluronic L10 significantly decreased the surface tension, especially at a ratio of 0.2, where this value decreased by 27% (p<0.0001) (FIG. 1B). This led to a significant decrease in the signal decay over time resulting in a stability increase of 39% (p<0.0001) (FIG. 2C-D). The Pluronic had little impact on size; NBs had an average diameter of 208±21.3 nm.

Example 2

Figure 2B:
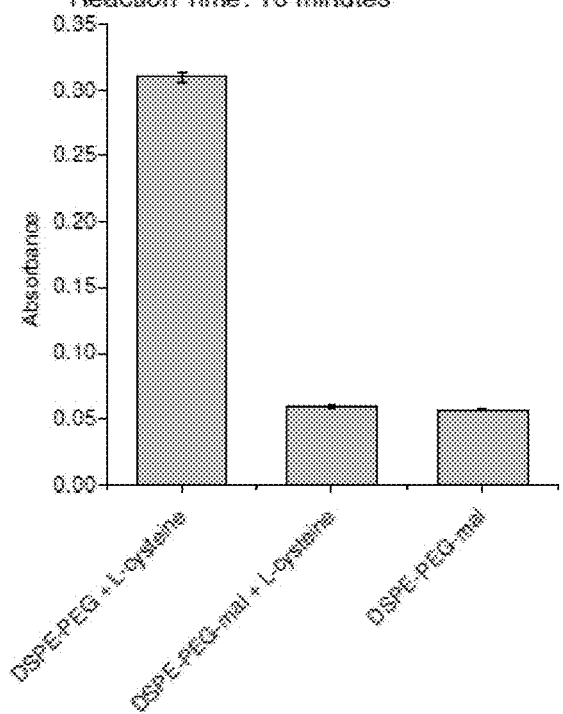

Characterization of PSMA-1-Cys Peptide Synthesis and Lipid Conjugation Via MALDI-TOF and Ellman's Analysis The lipids (DSPE-PEG, DSPE-PEG-MAL) and L-cysteine were dissolved in 0.1M phosphate buffer. L-cysteine was added to the DSPE-PE and DSPE-PEG-MAL groups and the samples were evaluated for thiol content using Ellman's assay. Two different MAL:Thiol ratios were used (2:1 and 2:0.5). It is evident from FIG. 2A, that the reaction takes place rapidly, and no change is seen after 10 minutes. The level of thiol groups in the 2:0.5 ratio group decreased to control levels after 10 min (FIG. 2B), indicating near complete binding of cysteine to the DSPE-PEG-MAL group. Characterization of PSMA-1-cys peptide synthesis and lipid conjugation to PSMA-1-cys was confirmed by Matrix Assisted Laser.

Example 3

Figure 3A:
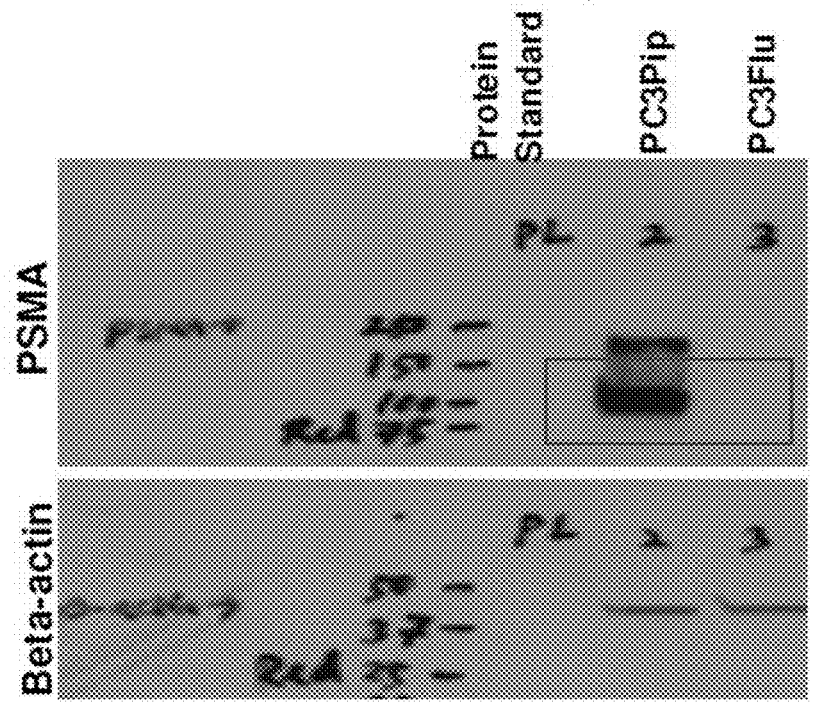
FIGS. 3(A-B) illustrate images showing PSMA expression in cells (A) and tumors (B).
Figure 3B:
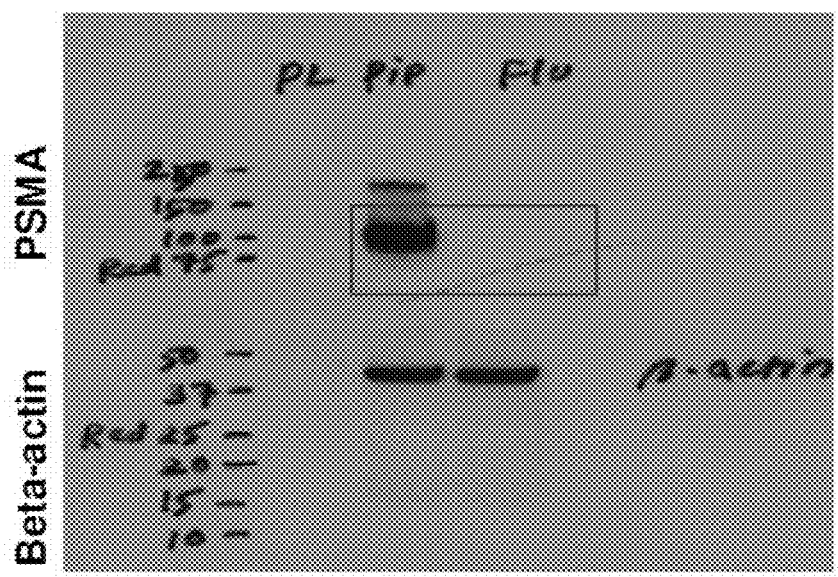

Confirmation of PSMA Biomaker Expression in Cell Lines Via Western Blotting
Methods PC3pip (PSMA positive) and PC3Flu (PSMA negative) cells were grown to the logarithmic phase, rinsed with phosphate-buffered saline (PBS), placed on ice, and suspended in 200 µl of radioimmunoprecipitation assay (RIPA) protein lysis buffer. Next, all cells/tumor lysates were transferred to a 1.5-mL tube and centrifuged at 12000 rpm and 4° C. for 15 min. The resulting supernatant was transferred to a new 1.5 mL centrifuge tube. A bicinchoninic acid (BCA) kit was then used to determine the protein concentration. Additionally, the samples were supplemented with 2× Laemmli loading buffer, mixed and boiled for 5 min to fully denature the proteins. Twenty micrograms of total protein was separated via SDS-PAGE and transferred to a nitrocellulose membrane via the semi-dry blotting method. Membranes were blocked with 5% milk in Tris Buffered Saline-Tween 20 (TBST) for 1 hour at room temperature. PSMA was detected with mAb J591 0.2 mg/mL for 1 hour followed by incubation with horseradish peroxidase-goat-anti-mouse IgG antibody (1:5,000 dilution) for 1 hour. After 3 TBST washes, blots were visualized by chemiluminescence. FIG. 3 confirms expression of PSMA in both the PC3pip cell line as well as tumors grown from PC3pip cells. Lack of expression is seen in the PC3flu lines in both experiments.

Example 4

Competition Binding Assay
Methods

Figure 4:
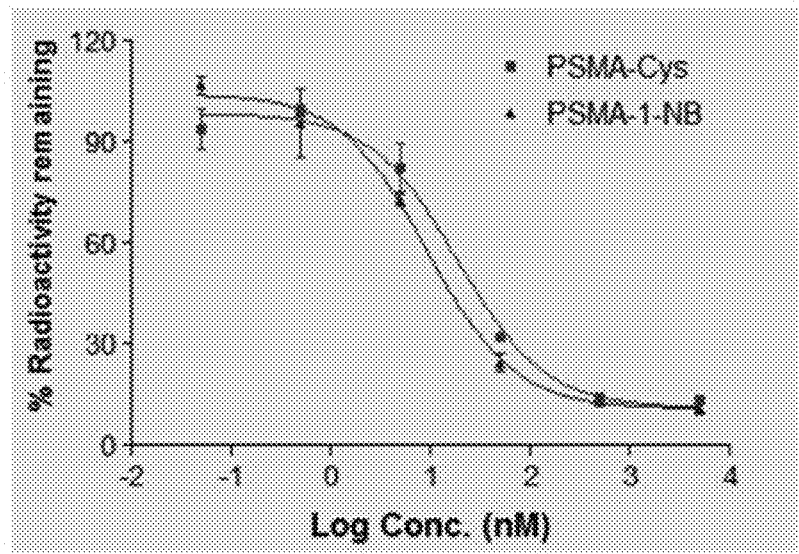
FIG. 4 illustrates a plot showing competitive binding assay of PSMA-1 conjugated nanobubbles and PSMA-Cys.

Cells ($5\times10^5$) were incubated with free PSMA-cys/PSMA-1-NB and N—[N—[(S)-1,3-dicarboxypropyl]carbamoyl]-S-[3H]-methyl-L-cysteine (3H-ZJ24; GE Healthcare Life Sciences) in a total volume of 200 mL of 50 mmol/L Tris (pH 7.5) for 1 hour at 37° C. The mixture was centrifuged at 3,000 g for 5 minutes at 4 deg C. to separate bound and free 3H-ZJ24. The supernatant was removed, and the cell pellet was washed 3 times with 500 mL of cold Tris buffer. Four milliliters of ECOLUME scintillation cocktail (MP Biomedicals) was added, and radioactivity was counted. Data were analyzed using GraphPad Prism 3.0.
Results Results show that the IC50 of PSMA-1-NB is lower (9.2 nM) than the ligand PSMA-1 (18.6 nM) (FIG. 4) in PSMA positive LNCaP cells.

Example 5

In Vitro Binding Studies (Optimization of Ligand Density and Cell Microscopy)
Methods Lipid conjugation of PSMA-Cys was performed through the —SH group of cysteine. PSMA-Cys was dissolved in anhydrous DMSO, to which 2.5-fold excess amount of Maleimide-PEG(2k)-DSPE was added. To formulate NBs, lipids DPPC, DPPE, DPPA and DSPE-PEG-PSMA-1 were dissolved in chloroform at a 4:1:1:1 ratio, dried and hydrated in PBS with Pluronic L10 solution. For optimization of binding, 40,000 cell/well were seeded 24 hr. before experiments. Bubbles with varying amounts of PSMA-cys ligand (0, 5, 25 and 50 µg (by weight)) were added and incubated for 15, 30 and 60 min. Rhodamine-DSPE was used to label to NBs. Cells were then washed with PBS and fluorescence per well analyzed with a plate reader.

Figure 5:
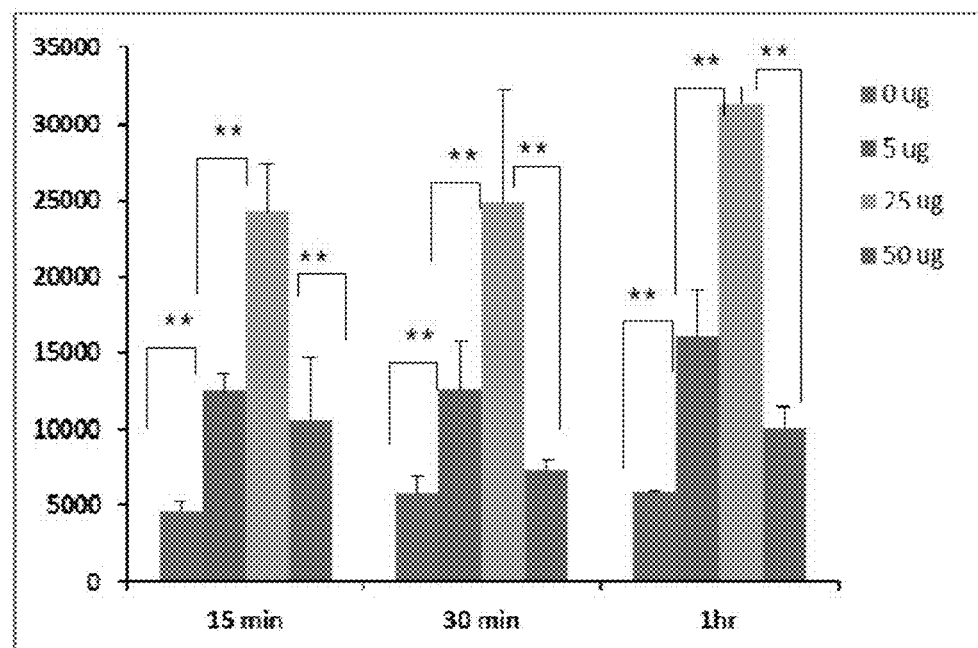
FIG. 5 illustrates a graph showing binding optimization of PSMA-1-nanobubbles labeled with rhodamine in PC3pip cells.
Figure 6A:
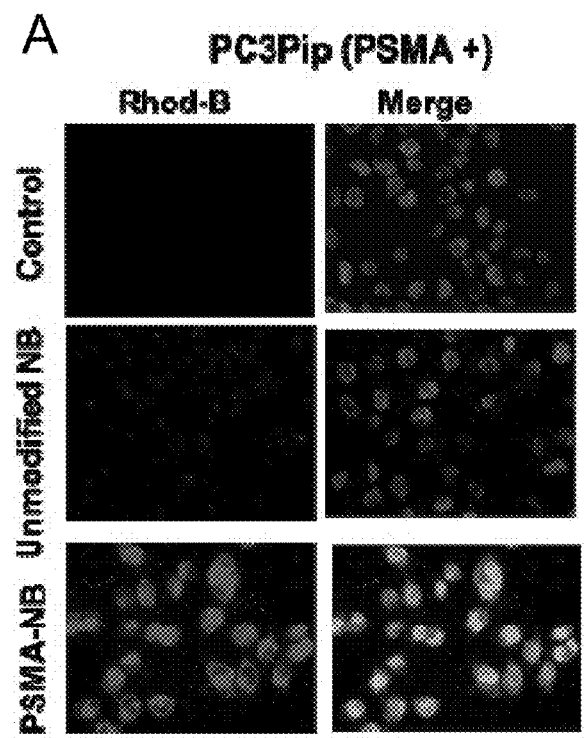
FIGS. 6(A-C) illustrate images and a graph showing binding of PSMA-1-nanobubbles (fluorescence and rhodamine-DSPE) in PC3pip cells (A) and PC3flu cells (B) and the respective quantification of microscopy data (C).
Figure 6B:
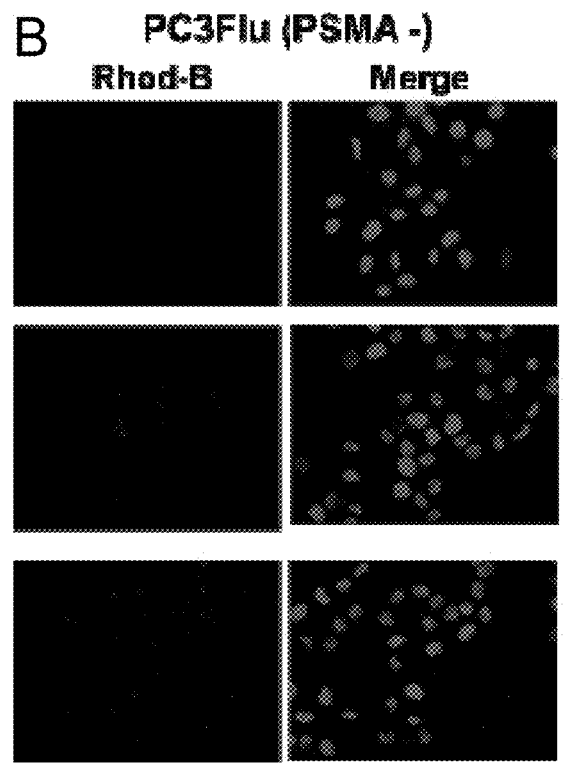
Figure 6C:
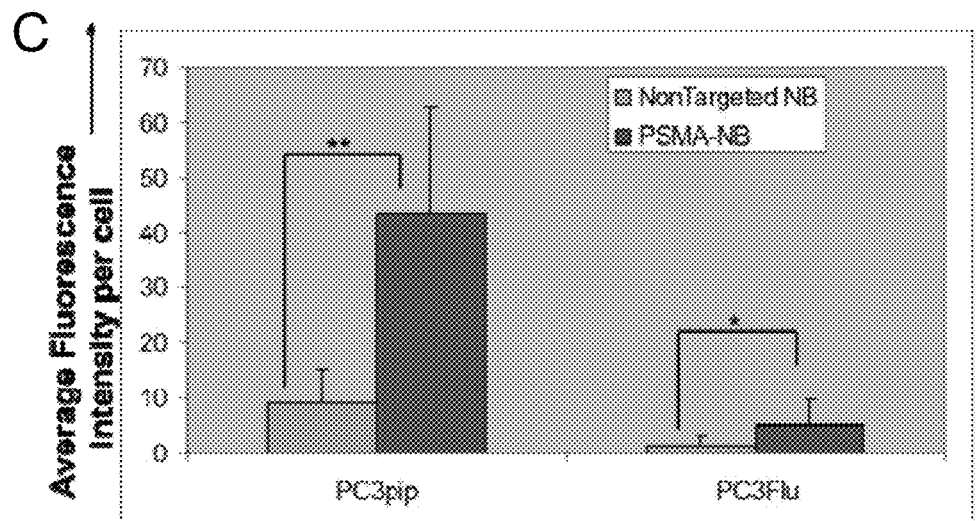
Figure 7A:
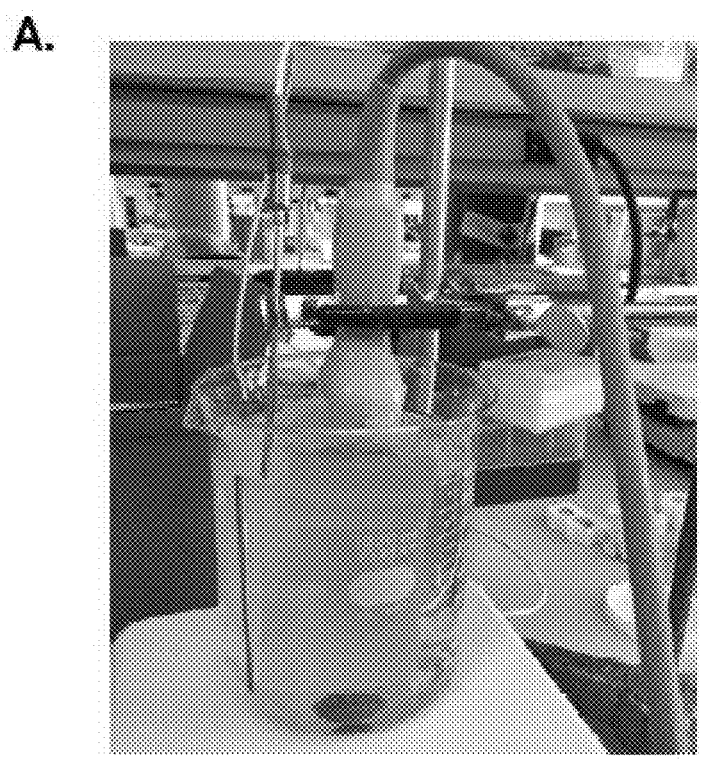
FIGS. 7(A-D) illustrate images and plots showing: (A) acoustic characterization of nanobubbles in a phantom setup, (B) images acquired with clinical ultrasound, results of experiments comparing the signal intensity (C) and signal decay (D) for PSMA and Cy5.5 functionalized and non-functionalized nanobubbles.
Figure 7B:
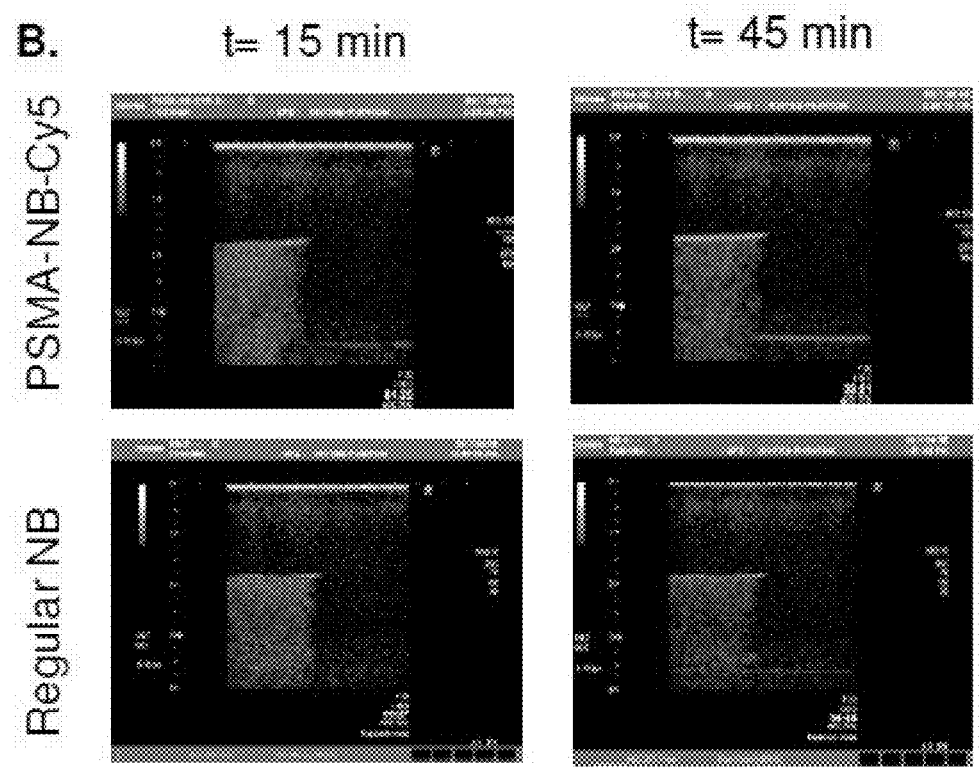
Figure 7C:
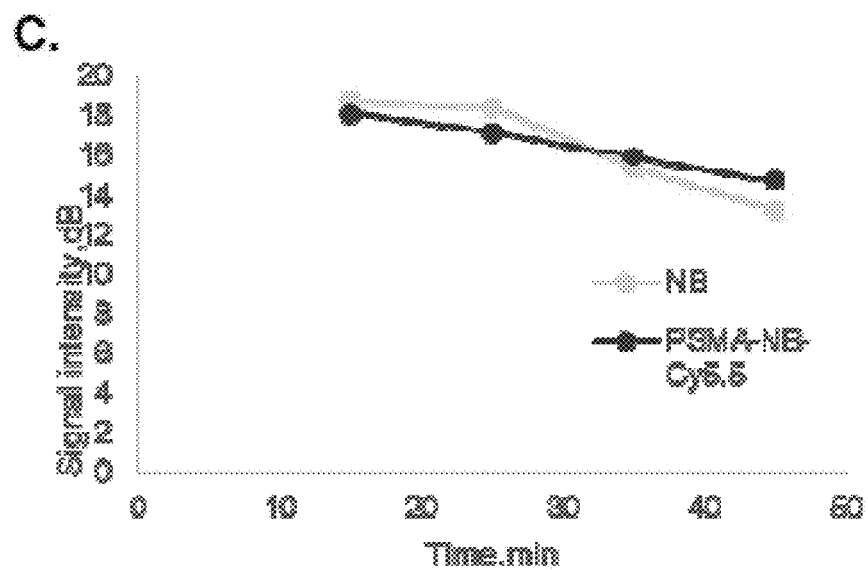
Figure 7D:
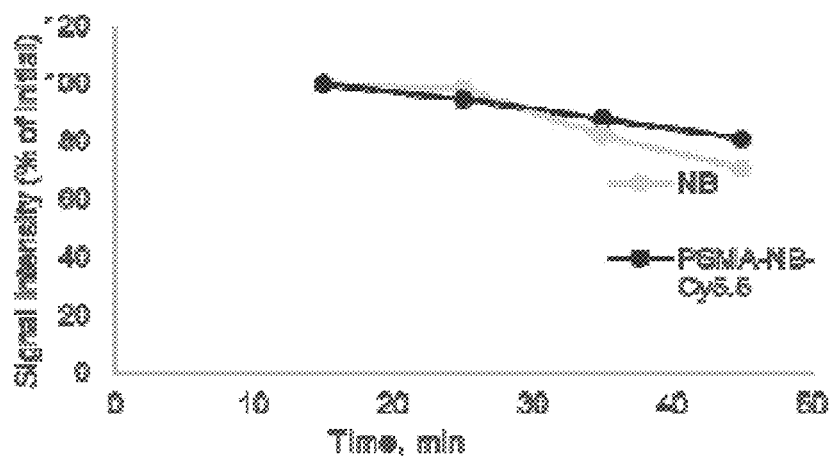

For microscopy studies, 800,000 cells were seeded in 35 mm dish 24 hr before the experiment. Each dish contained one glass cover slip. On the day of experiment cells were washed by PBS for at least 2 times. Then the cells were incubated at 37° C. either with unmodified or modified NBs for an hour. Cells were washed 2 times with PBS after incubation and fixed with 4% paraformaldehyde for 10 min. The cover slips were transferred to new dish and washed again for 3 times with PBS. Finally cell nucleus was tagged with DAPI and slides were prepared with the cover slips. Image was taken with LEICA fluorescence microscope 25×.
Results NBs were fluorescently tagged by adding rhodamine-DSPE into the lipid film. As evident in FIG. 5 nanobubbles containing 25 µg of PSMA-cys are better in targeting than other formulations. To determine cell binding, PSMA-expressing cells (PC3pip) and cells that do not express PSMA (PC3flu) were seeded ($1\times10^6$ cells) onto 35 mm dishes containing a cover slip 24 hrs prior to the experiment. Incubation of NBs with cells in culture for 60 min showed that targeted NBs accumulated significantly higher in PC3pip cells (FIG. 6). Data were collected using a fluorescent microscope and images processed to quantify fluorescence signal in cells. These preliminary in vitro data suggest that these PSMA-1 functionalized NBs indeed are able to bind cells expressing PSMA biomarker.

Example 6

Acoustic Characterization of PSMA-1-NB

Following conjugation of the PSMA-1-cys ligand to DSPE-PEG-MAL lipid, we formulated nanobubbles using standard procedures. Initially, we did not stabilize these with polymers, because we wanted to explore the simpler bubble formulation strategy. Nanobubbles were then assessed via ultrasound imaging for their initial signal intensity as well as signal decay over time.
Methods These experiments were conducted at physiological temperature, in a stirred system depicted in FIG. 7. Bubbles were diluted into the PBS bath, and US images were acquired at 1 frame every 10 seconds for the first 5 min, followed by periodic imaging for 30 minutes. A 12 MHz contrast harmonic imaging protocol was used, as described above. The decay and initial signal of functionalized nanobubbles also labeled with Cy5.5 fluorescent probe to that of standard, non-functionalized nanobubbles, to determine whether the surface decoration de-stabilized the bubbles or lead to a reduction in echogenicity.
Results Both bubble types showed good stability over time and a 20% signal decay over 45 minutes. There was no difference seen with functionalized bubbles. This suggests that the addition of PSMA-1 ligand and the fluorescent label do not alter the signal intensity or the stability of the nanobubbles.

Example 7

PSMA Expression In Vivo
Mouse Tumor Xenograft Models

All animal procedures were performed according to Institutional Animal Care and Use Committee (IACUA)-approved protocols. For flank tumor xenografts, 6- to 8-week-old athymic nude mice were implanted subcutaneously with $1 \times 10^6$ of PSMA-negative PC3flu and PSMA-positive PC3pip cells in 75 µL Matrigel on the right leg. Animals were observed every other day until tumors reached at about 5-6 mm in diameter. After 2 weeks, animals were ready for experiment.
In Vivo Imaging Studies Imaging was performed with the aid of the Maestro Imaging System (Perkin-Elmer) with each mouse receiving 1 nmol of NIR probe in PBS through tail vein injection. Imaging was performed at different time points using the appropriate filter set (deep red filter set for PSMA-1-IR800). During imaging, the temperature of imaging bed was adjusted to 37° C. Mice received inhalation of isofluorane through a nose cone attached to the imaging bed. Mice were imaged over 24 hr post injection.

Figure 8:
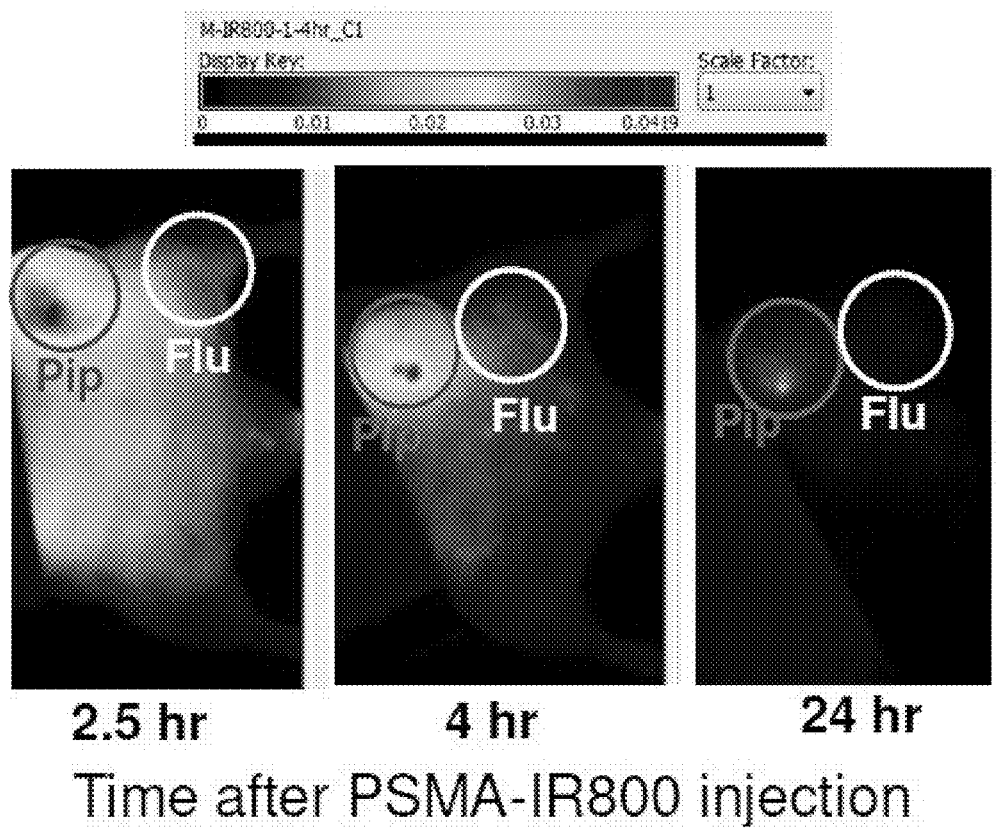
FIG. 8 illustrates images of PC3pip and PC3flu tumors grown adjacent to each other in mouse flank following IV injection of fluorescent PSMA-1 (without nanobubbles).

Results are shown in FIG. 8. The PSMA-1-IR800 can be seen accumulating in the Pc3pip tumors but not in the Pc3flu tumors. The peak accumulation was at 2.5 hours following injection. This experiment confirmed that the tumors express the biomarker and can be imaged with optical imaging. Next steps include repeating these experiments with fluorescent PSMA-1-NBs. These studies are currently in the planning stages and will commence later this year.

Example 8

Nanobubbles Enhance Ultrasound Imaging of Prostate Tumors in Mice

Figure 9A:
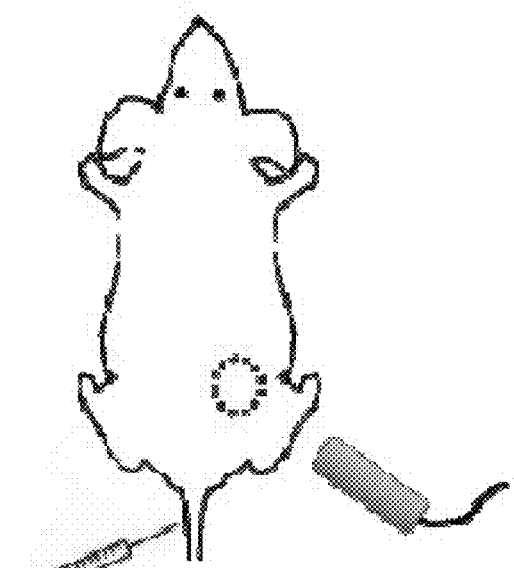
FIGS. 9(A-D) illustrate: (A) a schematic drawing of an animal tumor model and ultrasound scan orientation, (B) images comparing microbubbles and nanobubbles in PC3 flank tumor 15 seconds after contrast injection, (C) representative tumor images of nanobubbles and microbubbles from the same mouse, and (D) mean TIC curves for nanobubbles and microbubbles.
Figure 9B:
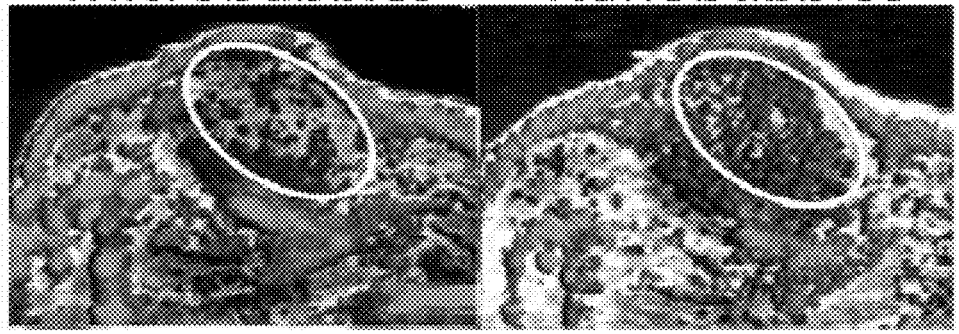
Figure 9C:
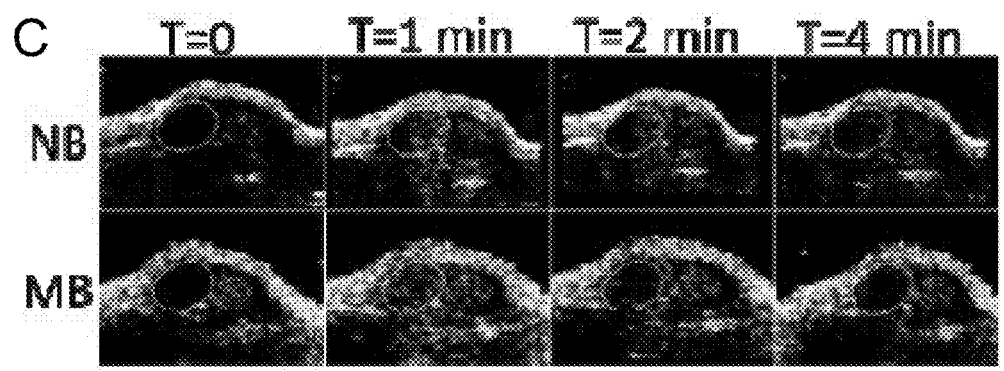
Figure 9D:
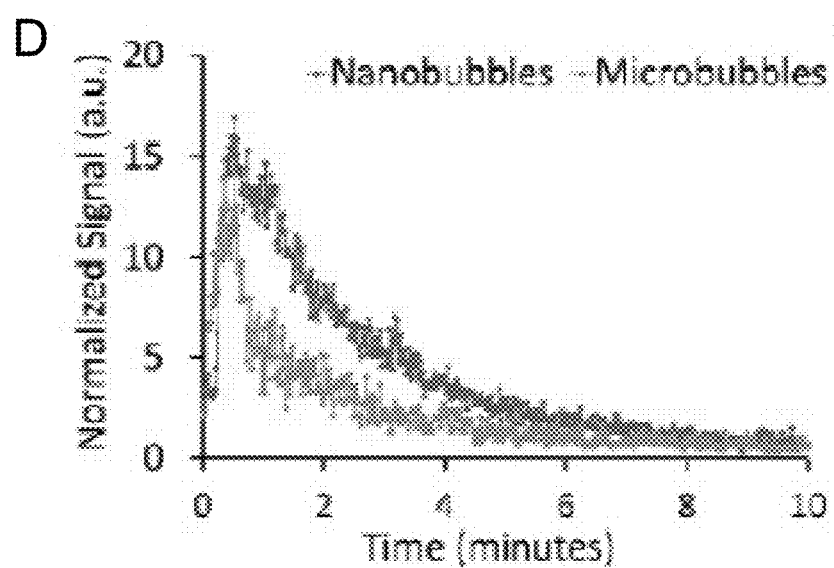

The most widely used ultrasound contrast agents are lipid or protein-stabilized perfluorocarbon (PFC) gas microbubbles (MB) typically exceeding 2 µm in diameter. These bubbles usually show rapid transient tumor enhancement, as they are confined to vasculature. To achieve longer lasting enhancement and improved delineation of tumors, we developed sub-micron lipid and surfactant-stabilized PFC nanobubbles (NB). Here, we compared tumor kinetics of the NBs compared to commercially available MBs.
Methods $C_3F_8$ NBs were formulated by dissolving a cocktail of lipids including DBPC, DSPE-PEG in PBS followed by gas exchange and activation via mechanical agitation. NBs were purified by centrifugation, and size was measured by dynamic light scattering (DLS). Tumors were inoculated in the flank of three male nude mice by injection of PC3 prostate cancer cells in Matrigel®, and grown to 5-8 mm (FIG. 9A). Contrast-enhanced US images were acquired with Vevo 3100 (Visualsonics Fujifilm) at 1 fps, 18 MHz, and 4% power following tail vein injections of 100 ul of either MicroMarker (Visualsonics) or NBs. Maximum intensity projection (MIP) and time-intensity curves (TIC) were obtained in the same mouse for both contrast agents.
Results NBs have a diameter of 240±95 nm, (compared to 2-3 µm for MicroMarker). MIP images (FIG. 9B) show that NB provided more signal throughout the tumor cross section compared to MBs at t=15 s. Representative contrast images are shown in FIG. 9C and the mean TIC for all replicates is shown in FIG. 9D. NBs had a half-life of 2.1 min compared to 1 min for microbubbles, and at t=2 min showed a signal intensity nearly 3 times higher than MBs. Higher tumor signal and slower wash out suggests that smaller NBs were able to penetrate out of the leaky tumor vasculature and further into the tumor interstitium. Such NBs may eventually provide a more effective contrast agent compared to MBs and could enhance US guided biopsies.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, the following is claimed:

1. A composition comprising:
a plurality of PSMA targeted nanobubbles, each PSMA targeted nanobubble including a membrane that defines at least one internal void, which includes at least one gas, and at least one PSMA ligand coupled to the membrane, the membrane further including at least one lipid and at least one nonionic triblock copolymer that is effective to control the size of the nanobubble without compromising in vitro and in vivo echogenicity of the nanobubble, the PSMA targeted nanobubbles upon intravenous administration to a subject having sizes effective to extravasate from vasculature into parenchyma of the subject; and
wherein the PSMA ligand has the following formula (I):

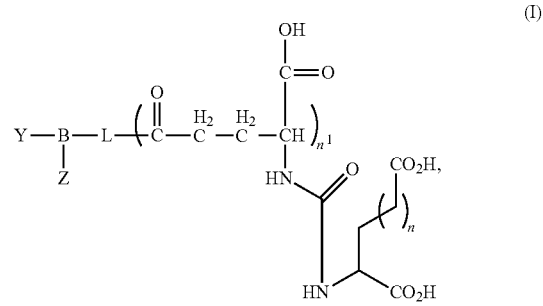

wherein:
n and $n^1$ are each independently 1, 2, 3, or 4;
L is an optionally substituted aliphatic or heteroaliphatic linking group;
B is a linker that includes at least one negatively charged amino acid; and
Y is a lipid of the nanobubble membrane, which is directly or indirectly coupled to B, and
Z is hydrogen or at least one of a detectable moiety or label or a therapeutic agent, which is directly or indirectly coupled to B.

2. The composition of claim 1, the at least one nonionic triblock copolymer being selected from the group consisting of poloxamers, poloxamines, meroxapols, and combinations thereof.

3. The composition of claim 1, the at least one nonionic triblock copolymer comprising the chemical formula of:

wherein a is from 2 to 130 and b is from 15 to 67.

4. The composition of claim 1, the nanobubbles having an average diameter of about 30 nm to about 400 nm.

5. The composition of claim 1, wherein the nanobubbles include an interpenetrating crosslinked biodegradable polymer.

6. The composition of claim 5, the interpenetrating crosslinked biodegradable polymer comprising a crosslinked acrylamide polymer.

7. The composition of claim 6, the crosslinked acrylamide polymer comprising the reaction product of N, N-diethyl acrylamide (NNDEA) and N, N-bis(acryoyl) cystamine (BAC).

8. The composition of claim 1, wherein the at least one lipid comprises a mixture of at least two of 1,2-Dipalmitoyl-sn-Glycero-3-Phosphocholine (DPPC), 1,2 Dipalmitoyl-sn-Glycero-3-Phosphate (DPPA), 1,2-dipalmitoyl-sn-glycero-3-phosphoethanolamine (DPPE) 1,2-Distearoyl-phosphatidylethanol amine-methyl (DSPE), or 1,2-dibehenoyl-sn-glycero-3-phosphocholine (DBPC).

9. The composition of claim 1, wherein the PSMA ligand is covalently linked to at least one lipid of the membrane.

10. A method for delineating prostate cancer cells in a region of interest (ROI) of a subject in need thereof, the method comprising the steps of:
administering to the subject a plurality of PSMA targeted nanobubles, each PSMA targeted nanobubble including a membrane that defines at least one internal void, which includes at least one gas, and at least one PSMA ligand coupled or conjugated to the membrane, the membrane further including at least one lipid and at least one nonionic triblock copolymer that is effective to control the size of the nanobubble without compromising in vitro and in vivo echogenicity of the nanobubble, the PSMA targeted nanobubbles upon intravenous administration to the subject having sizes effective to extravasate from vasculature into parenchyma of the subject, wherein the PSMA ligand has the following formula (I):

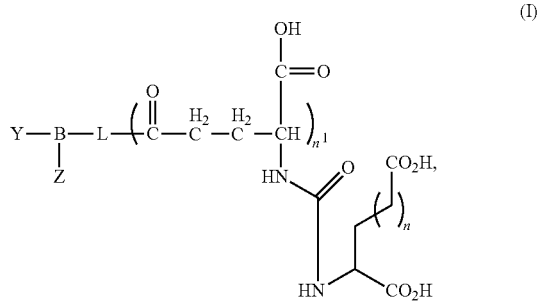

wherein:
n and $n^1$ are each independently 1, 2, 3, or 4;
L is an optionally substituted aliphatic or heteroaliphatic linking group;
B is a linker that includes at least one negatively charged amino acid; and
Y is a lipid of the nanobubble membrane, which is directly or indirectly coupled to B, and
Z is hydrogen or at least one of a detectable moiety or label or a therapeutic agent, which is directly or indirectly coupled to B; and
generating at least one image of the ROI by ultrasound imaging the nanobubbles in the ROI to delineate prostate cancer cells.

11. The method of claim 10, the at least one nonionic triblock copolymer being selected from the group consisting of poloxamers, poloxamines, meroxapols, and combinations thereof.

12. The method of claim 11, the at least one nonionic triblock copolymer comprising the chemical formula of:

$$HO-(C_2H_4O)_a(C_3H_6O)_b(C_2H_4O)_a-H,$$

wherein a is from 2 to 130 and b is from 15 to 67.

13. The method of claim 10, the nanobubbles having an average diameter of about 30 nm to about 400 nm.

14. The method of claim 10, wherein the nanobubbles include an interpenetrating crosslinked biodegradable polymer.

15. The method of claim 14, the interpenetrating crosslinked biodegradable polymer comprising a crosslinked acrylamide polymer.

16. The method of claim 15, the crosslinked acrylamide polymer comprising the reaction product of N, N-diethyl acrylamide (NNDEA) and N, N-bis(acryoyl) cystamine (BAC).

17. The method of claim 10, wherein the at least one lipid comprises a mixture of at least two of 1,2-Dipalmitoyl-sn-Glycero-3-Phosphocholine (DPPC), 1,2 Dipalmitoyl-sn-Glycero-3-Phosphate (DPPA), 1,2-dipalmitoyl-sn-glycero-3-phosphoethanolamine (DPPE) 1,2-Distearoyl-phosphatidylethanol amine-methyl (DSPE), or 1,2-dibehenoyl-sn-glycero-3-phosphocholine (DBPC).

18. The method of claim 10, wherein the PSMA ligand is covalently linked to at least one lipid.

* * * * *